US012620471B2

(12) United States Patent
Kyyrö et al.

(10) Patent No.: US 12,620,471 B2
(45) Date of Patent: May 5, 2026

(54) APPLICATION TONALITY ADJUSTMENT MODEL

(71) Applicant: Oura Health Oy, Oulu (FI)

(72) Inventors: Mats Kyyrö, Oulu (FI); Antonio Gusmao, Oulu (FI); Kathryn LaBeaume, Boise, ID (US); Marcin Banaszynski, Rybnik (FI); Josh Mobley, Clayton, NC (US); Kathryn Berry, San Francisco, CA (US); Kelsey Radloff, San Rafael, CA (US); Mari Pauliina Karsikas, Oulu (FI); Johanna Leena Kyllikki Still, Oulu (FI); Sofia Strömmer, Oulu (FI); Shishir Bhattarai, Helsinki (FI); Kaisa Helena Tarvainen, Oulu (FI); Daria Kalmykova, Espoo (FI); Marko Uusitalo, Oulu (FI); Tarja Karjalainen, Oulu (FI); David Lee Hwang, Pleasant Hill, CA (US); Michael Johnson, Township of Washington, NJ (US)

(73) Assignee: Oura Health Oy, Oulu (FI)

( * ) Notice: Subject to any disclaimer, the term of this patent is extended or adjusted under 35 U.S.C. 154(b) by 285 days.

(21) Appl. No.: 18/478,073

(22) Filed: Sep. 29, 2023

(65) Prior Publication Data

US 2025/0111919 A1 Apr. 3, 2025

(51) Int. Cl.
| G16H 20/30 | (2018.01) |
| G16H 40/67 | (2018.01) |
| G16H 50/20 | (2018.01) |

(52) U.S. Cl.
CPC ............. *G16H 20/30* (2018.01); *G16H 40/67* (2018.01); *G16H 50/20* (2018.01)

(58) Field of Classification Search
CPC ......... G16H 20/30; G16H 40/67; G16H 50/20
See application file for complete search history.

(56) References Cited

U.S. PATENT DOCUMENTS

2018/0375807 A1* 12/2018 Krans ..................... H04L 51/02
2021/0012881 A1* 1/2021 Queenan ................ G16H 50/70

OTHER PUBLICATIONS

Jabil Inc., "Smart Ring Demonstrator," 2022, jabil.com/healthcare (Year: 2022).*

* cited by examiner

*Primary Examiner* — Rachelle L Reichert
*Assistant Examiner* — Amanda R. Covington
(74) *Attorney, Agent, or Firm* — ArentFox Schiff LLP

(57) ABSTRACT

Methods, systems, and devices for adjusting a messaging tonality of messages delivered to a user are described. The system may acquire baseline physiological data measured from the user and generate one or more messages based on the baseline physiological data and in accordance with a first messaging tonality. The system may acquire additional physiological data from the user based on providing the one or more messages. In some cases, the system may perform an evaluation of the first messaging tonality by comparing the additional physiological data with the baseline physiological data and select a second messaging tonality from a plurality of messaging tonalities based on the evaluation of the first messaging tonality. The system may generate one or more additional messages to be provided to the user in accordance with the second messaging tonality based on selecting the second messaging tonality.

20 Claims, 9 Drawing Sheets

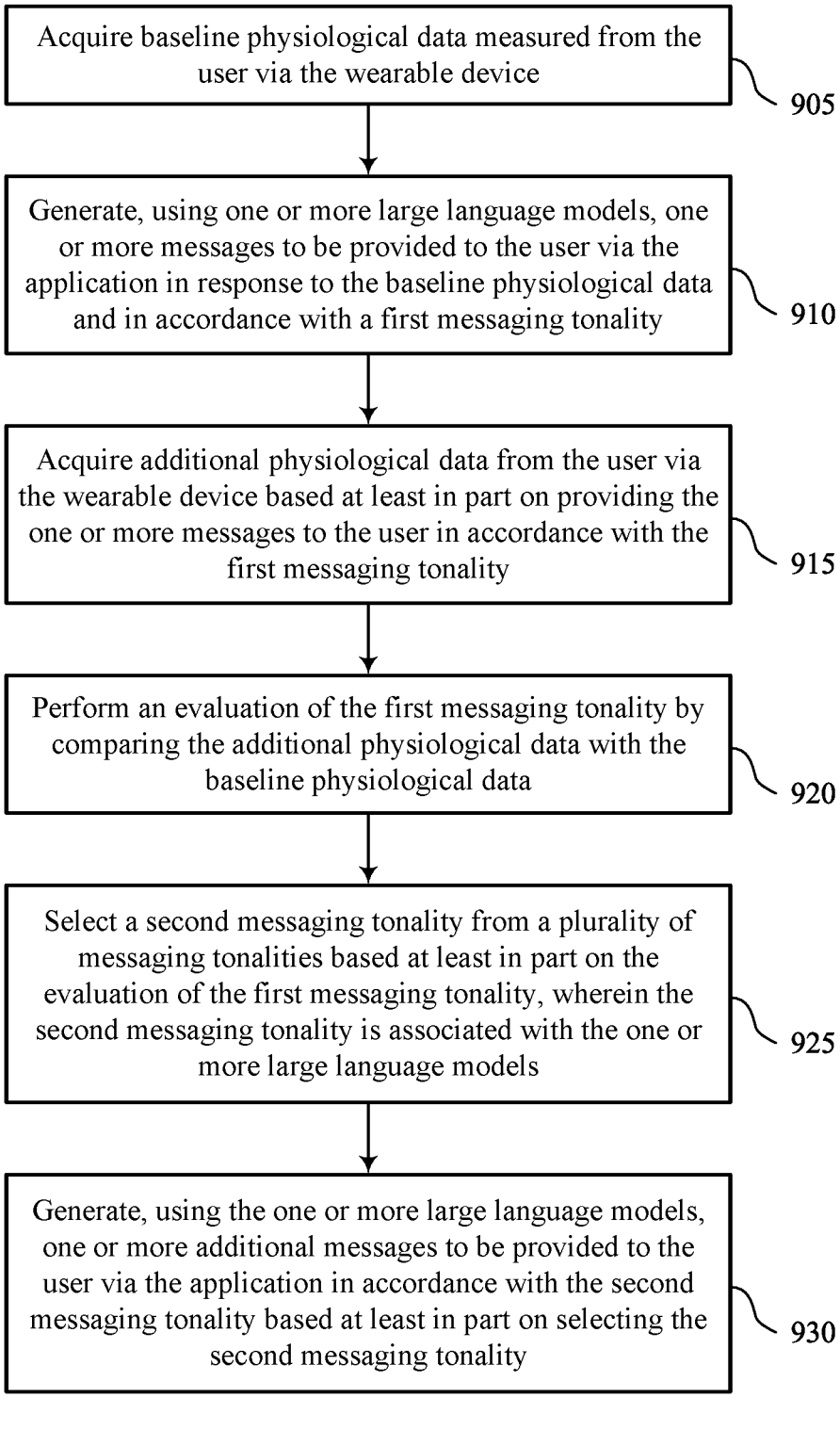

Acquire baseline physiological data measured from the user via the wearable device — 905

Generate, using one or more large language models, one or more messages to be provided to the user via the application in response to the baseline physiological data and in accordance with a first messaging tonality — 910

Acquire additional physiological data from the user via the wearable device based at least in part on providing the one or more messages to the user in accordance with the first messaging tonality — 915

Perform an evaluation of the first messaging tonality by comparing the additional physiological data with the baseline physiological data — 920

Select a second messaging tonality from a plurality of messaging tonalities based at least in part on the evaluation of the first messaging tonality, wherein the second messaging tonality is associated with the one or more large language models — 925

Generate, using the one or more large language models, one or more additional messages to be provided to the user via the application in accordance with the second messaging tonality based at least in part on selecting the second messaging tonality — 930

APPLICATION TONALITY ADJUSTMENT MODEL

FIELD OF TECHNOLOGY

The following relates to wearable devices and data processing, including techniques for an application tonality adjustment model.

BACKGROUND

Some wearable devices may be configured to collect data from users including photoplethysmogram (PPG) data, heart rate data, and the like. Some wearable devices may be associated with an application on a user device that generates messages and/or insights for the user based on the acquired physiological data.

BRIEF DESCRIPTION OF THE DRAWINGS

FIG. 9 shows a flowchart illustrating methods that support application tonality adjustment model in accordance with aspects of the present disclosure.

DETAILED DESCRIPTION

Figure 1:
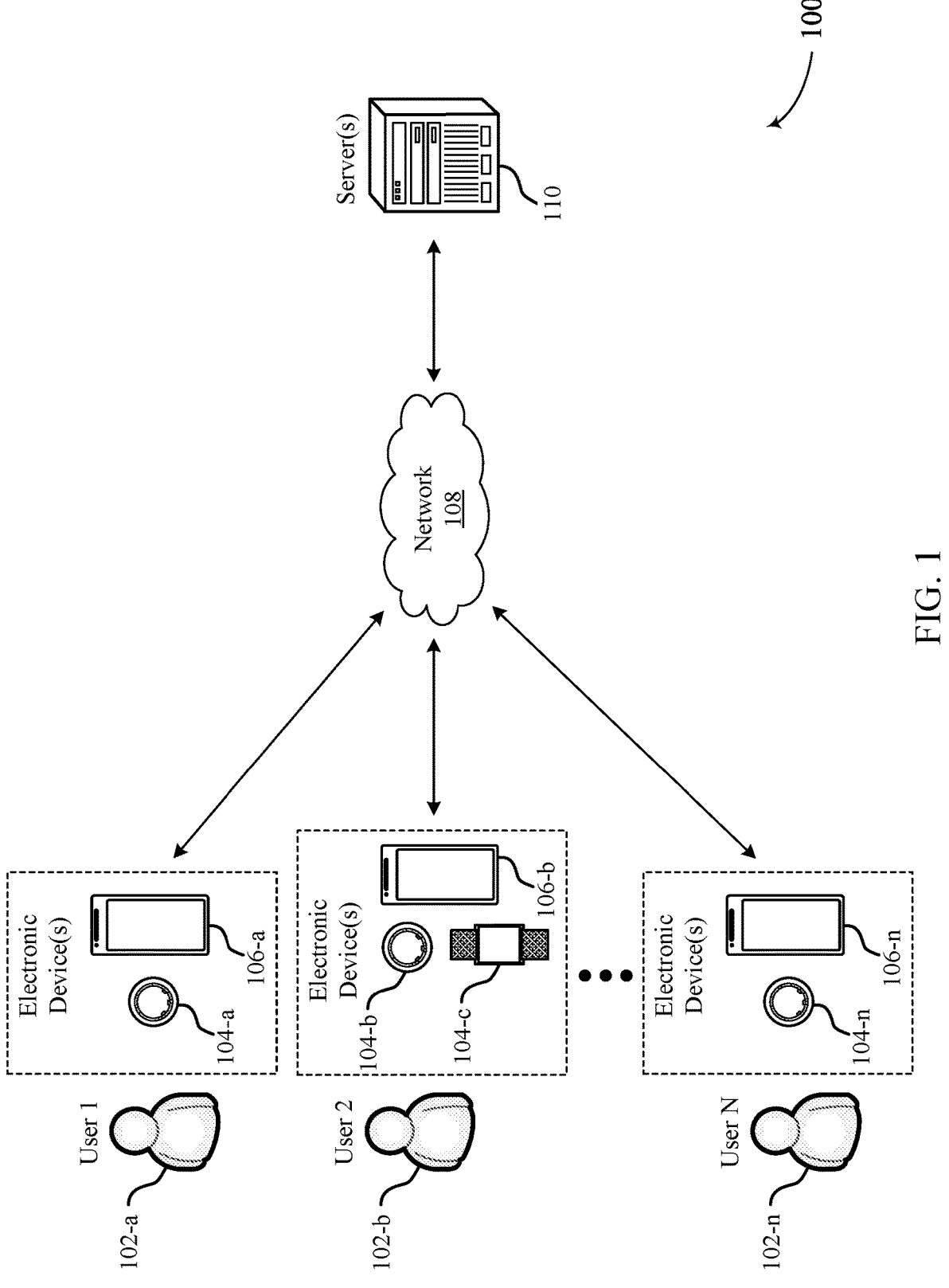
FIG. 1 illustrates an example of a system that supports techniques for an application tonality adjustment model in accordance with aspects of the present disclosure.

Some wearable devices may be configured to acquire physiological data from a user, including photoplethysmogram (PPG) data, temperature data, heart rate, heart rate variability (HRV) data, sleep data, respiratory data, blood pressure data, and the like. Acquired physiological data may be used to analyze behavioral and physiological characteristics associated with the user, such as movement, sleeping patterns, and the like. Many users have a desire for more insight regarding their physical health, including their activity patterns, sleep patterns, and overall physical well-being.

In some cases, wearable devices may be associated with an application on a user device that generates messages and/or insights for the user based on the acquired physiological data. However, conventional techniques that provide messages and/or insights to the user may utilize a same tone and/or content of the message for every user. That is, any user that exhibits physiological data that satisfies certain thresholds or characteristics may receive a message that is delivered with the same messaging tonality (e.g., "an encouraging coach" tonality). The content of messages delivered within the application may vary based on each respective user's physiological data, but existing applications may not allow the messaging tonality to vary from user to user. That is, even for devices that collect a user's physiological data, typical devices and applications lack the ability to collect other physiological, behavioral, or contextual inputs from the user that can be combined with the measured data to more comprehensively understand the complete set of physiological contributors to a user's health. Moreover, existing applications do not allow the messaging tonality to vary from user to user. Due to the fact that different users may react differently to various messaging tonalities, the inability to tailor messaging tonalities to each respective user may result in a lack of engagement and may affect a user's ability and motivation to improve their overall health.

Accordingly, aspects of the present disclosure are directed to techniques for adjusting the tonality of messages delivered to the user to determine which messaging tonality the user best responds to (e.g., which tonality results in an improved and/or maintained health outcome). For example, the system may generate, using one or more large language models (LLMs), one or more messages to be provided to the user via the application in accordance with a first messaging tonality and in response to baseline physiological data of the user. The system may acquire additional physiological data from the user via the wearable device after providing the one or more messages to the user in accordance with the first messaging tonality. In some cases, the system may perform an evaluation of the first messaging tonality by comparing the additional physiological data with the baseline physiological data. In other words, the effectiveness (or lack thereof) of the first messaging tonality may be evaluated by determining how, or whether, the user's physiological data changed as a result of the first messaging tonality. The system may select a second messaging tonality from a plurality of messaging tonalities based on the evaluation of the first messaging tonality and generate messages in accordance with the second messaging tonality.

The system may evaluate how the user's actions and physiological data change when messages are delivered according to different tonalities to identify which messaging tonality best suits the user. Subsequently, the application may use the identified messaging tonality to deliver messages to the user going forward. In such cases, the application may evaluate how the user's behaviors and physiological data react to different messaging tonalities and adapt the tonality to achieve certain goals. In this regard, messaging tonalities may be tailored for each respective user. In some cases, an application associated with a wearable device may test out different messaging tonalities for delivering messages to a user in order to determine which particular tonality increases a certain health outcome for the user. That is, the system may perform a trial and error of testing tonalities to see which tonality yields the best results, and/or may tailor the tonality to the user's physiological data and/or data trends. For example, if the user is meeting their goals, the tonality may be an upbeat and encouraging tone as compared to if the user is not meeting their goals, the tonality may be a tone with more empathy. In such cases, the tonality may be adjusted based on past, present, and/or future physiological data.

For purposes of the present disclosure, the term "tonality," "messaging tonality," "tone," "message tone," and the like terms, may be used to refer to the language/words of a delivered message, volume, cadence, inflection, punctuation, use of symbols, and the like. Messaging tonalities may vary in a range of empathetic to rational and/or formal to casual (e.g., may vary from "drill sergeant" tonality to "empathetic instructor" tonality). In some cases, messages may be delivered in accordance with different tonalities visually (e.g., written messages) and/or audibly (e.g., audio messages) by using adjusting multiple parameters of the delivered message, including the language/words of the message, volume, cadence, inflection, punctuation, use of symbols or emojis, and the like. For example, a first message delivered in accordance with a first tonality may read or voice "If this feels like a day for a new challenge, go for it," while a second message delivered in accordance with a second tonality may read or voice "Get out of bed and seize the day!"

The application may utilize machine learning models (e.g., natural language processing models) to generate sets of messages associated with different tonalities without changing the underlying guidance itself. Other application platforms may allow users to manually select different messaging personalities and/or tones. However, users may not always select the messaging tonality that most suits them. Moreover, other applications may lack the context of what has happened or is happening in the user's life to be able to dynamically adjust the tone (e.g., personality) of the messaging to improve a health outcome. Comparatively, by evaluating how a user's behaviors and physiological data react to different messaging tonalities, techniques described herein may be able to objectively identify the messaging tonality that works for each respective user. As such, techniques described herein may enable wearable applications to provide customized and personalized coaching guidance, recommendations, and insight into the user's overall health in a tone that the user is most receptive to in order to improve the overall health of the user.

Aspects of the disclosure are initially described in the context of systems supporting physiological data collection from users via wearable devices. Additional aspects of the disclosure are described in the context of an example graphical user interface (GUI). Aspects of the disclosure are further illustrated by and described with reference to apparatus diagrams, system diagrams, and flowcharts that relate to an application tonality adjustment model.

FIG. 1 illustrates an example of a system 100 that supports techniques for an application tonality adjustment model in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108 and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, which repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for adjusting a message tonality for a wearable device application. In particular, the system 100 illustrated in FIG. 1 may support techniques for delivering messages to the user 102 in accordance with one messaging tonality and switching to a different messaging tonality by evaluating the effect the messaging tonality has on the user's data (e.g., physiological data). Adjusting a messaging tonality of messages delivered to a user 102 may be performed by any of the components of the system 100, including the ring 104-a, the user device 106-a associated with User 1, the one or more servers 110, or any combination thereof.

For example, as shown in FIG. 1, User 1 (user 102-a) may be associated with a wearable device 104-a (e.g., ring 104-a) and a user device 106-a. In this example, the ring 104-a may collect baseline physiological data associated with the user 102-a, including PPG data, temperature, heart rate, HRV, respiratory rate, and the like. In some aspects, data collected by the ring 104-a may be used to determine the user's baseline physiological data. The system 100 may generate, using one or more LLMs, one or more messages to be provided to the user 102-a via an application and in accordance with a first messaging tonality. The ring 104-a may collect additional physiological data associated with the user 102-a based on providing the one or more messages to the user 102-a in accordance with the first messaging tonality. The system 100 may perform an evaluation of the first messaging tonality by comparing the additional physiological data with the baseline physiological data. In some cases, the system 100 may adjust the messaging tonality by selecting a second messaging tonality from a plurality of messaging tonalities based on the evaluation of the first messaging tonality. In such cases, the system 100 may generate, using the one or more LLMs, one or more additional messages to be provided to the user 102-a in accordance with the second messaging tonality.

In some implementations, the system 100 may generate alerts, messages, or recommendations for User 1, User, 2, and/or User N (e.g., via the ring 104-a, user device 106-a, or both) in accordance with the selected messaging tonality, where the messaging tonalities may vary in a range of empathetic to rational and/or formal to casual. In some cases, the messages may be delivered in accordance with different tonalities visually (e.g., written messages) and/or audibly (e.g., audio messages) by adjusting multiple parameters of the delivered message, including the language/words of the message, volume, cadence, inflection, punctuation, use of symbols, and the like. For example, a first message delivered in accordance with a first messaging tonality may read or voice "Need a new challenge? Looks like you've been less active than usual," while a second message delivered in accordance with a second messaging tonality may read or voice "Today could be the day to get up and get moving! Regular activity can help give you more energy and a better mood."

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
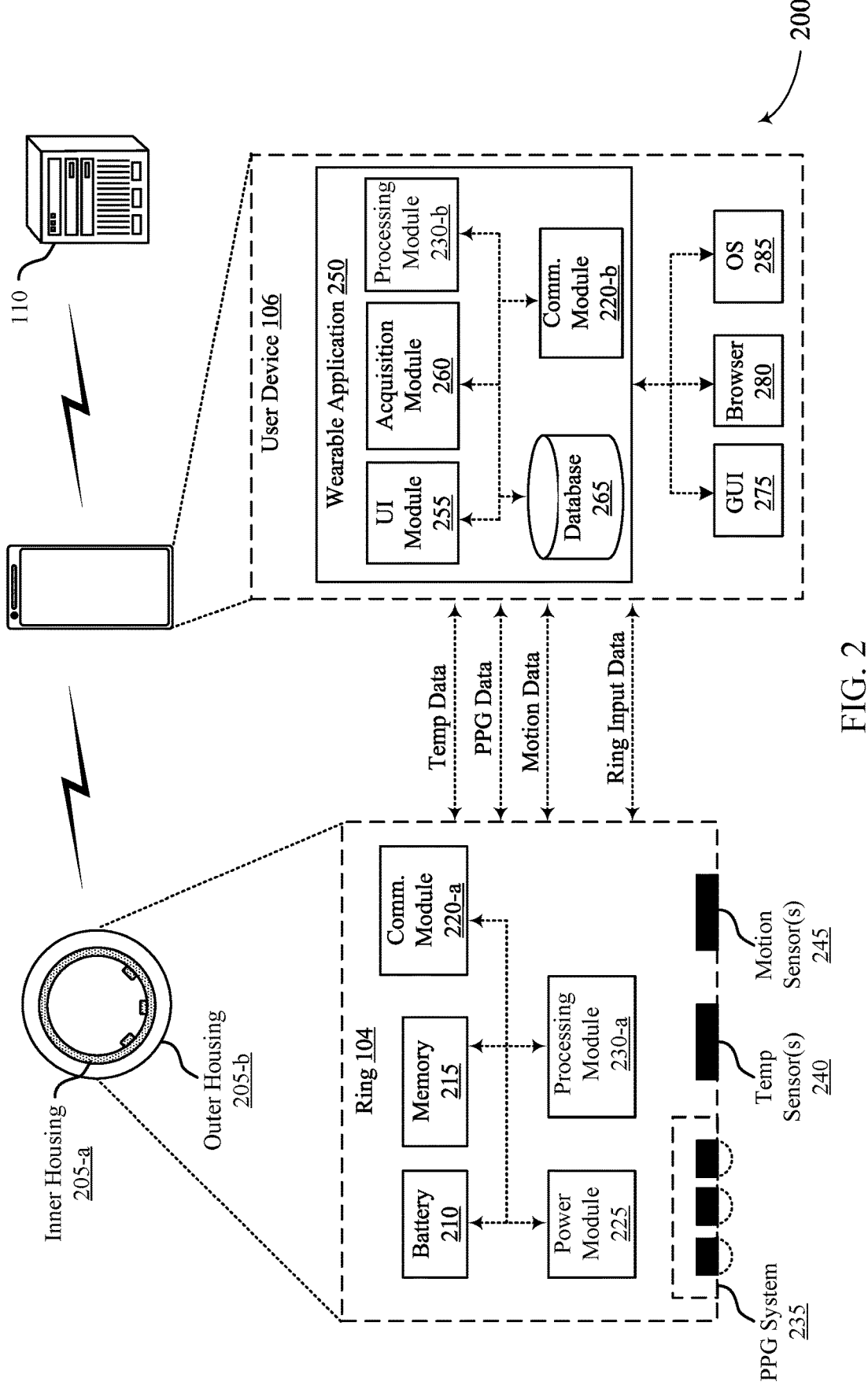
FIG. 2 illustrates an example of a system that supports techniques for an application tonality adjustment model in accordance with aspects of the present disclosure.

FIG. 2 illustrates an example of a system 200 that supports techniques for an application tonality adjustment model in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/ configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate (s) from water and/or other chemicals.

The outer housing 205-b may be fabricated from one or more materials. In some implementations, the outer housing 205-b may include a metal, such as titanium, which may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-b. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/ battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits.

Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage (s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalent of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed and may be calculated using the efficiency average of long sleep periods (e.g., primary sleep period) of the sleep day, weighted by a duration of each sleep period. The "restfulness" contributor may indicate how restful the user's sleep is and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for adjusting a messaging tonality of messages delivered to a user. In particular, the respective components of the system 200 may be used to select a messaging tonality from a plurality of messaging tonalities based on evaluating the effect that respective messaging tonalities have on the user's actions and/or physiological data. In some cases, the messaging tonality may be adjusted by leveraging sensors on the ring 104 of the system 200.

For example, as noted previously herein, the ring 104 of the system 200 may be worn by a user to collect data from the user, including PPG data, temperature, heart rate, HRV, respiratory data, sleep data, and the like. The ring 104 of the system 200 may collect the baseline physiological data and the additional physiological data from the user based on PPG sensors and measurements extracted from arterial blood flow (e.g., using PPG signals), capillary blood flow, arteriole blood flow, or a combination thereof. The baseline and/or additional physiological data may be collected continuously. In some implementations, the processing module 230-a may sample and/or receive the user's PPG signal continuously throughout the day and night. Sampling at a sufficient rate (e.g., one sample per second or one sample per minute) throughout the day and/or night may provide sufficient data for analysis described herein. In some implementations, the ring 104 may continuously acquire the PPG signal (e.g., at a sampling rate). In some examples, even though the PPG signal is collected continuously, the system 200 may leverage other information about the user that it has collected or otherwise derived (e.g., sleep stage, activity levels, illness onset, etc.) to select a representative PPG signal for a particular day that is an accurate representation of the underlying physiological phenomenon.

In contrast, systems that require a user to manually obtain their physiological data each day and/or systems that acquire physiological continuously but lack any other contextual information about the user may select inaccurate or inconsistent messaging tonalities, leading to decreased user experience. In contrast, data collected by the ring 104 may be used to accurately select a messaging tonality to help the user achieve certain goals. The system 200 may perform a trial and error of testing messaging tonalities to see which messaging tonality yields the best results, and/or may tailor the messaging tonality to the user's physiological data and/or data trends (e.g., if the user is meeting their goals the messaging tonality may be an upbeat and encouraging tone versus if the user is not meeting their goals the messaging tonality may be a tone with more empathy). Adjusting the messaging tonality and related techniques are further shown and described with reference to FIGS. 3 and 4.

Figure 3:
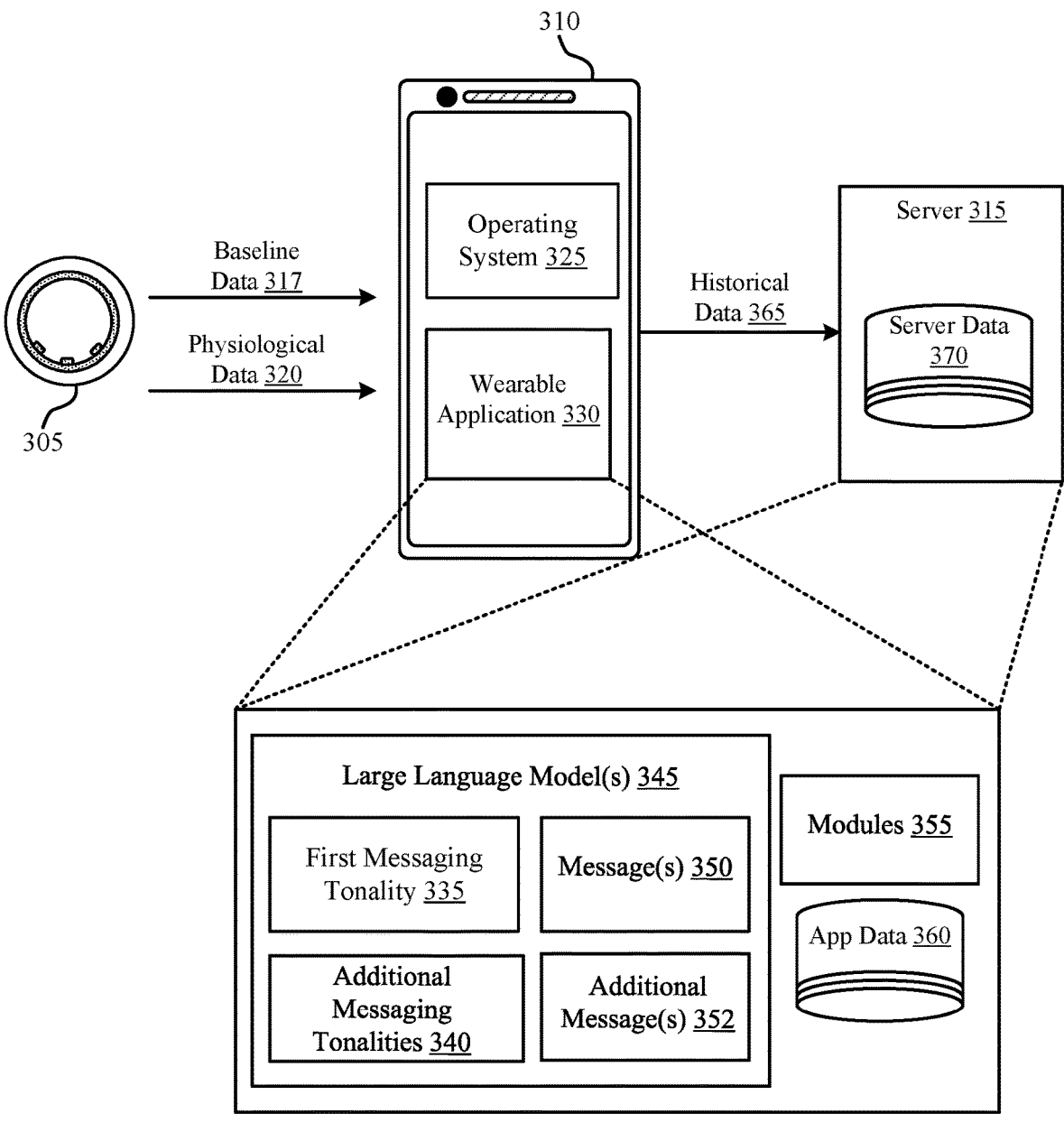
FIG. 3 shows an example of a system that supports techniques for an application tonality adjustment model in accordance with aspects of the present disclosure.

FIG. 3 shows an example of a system 300 that supports techniques for an application tonality adjustment model in accordance with aspects of the present disclosure. The system 300 may implement, or be implemented by, system 100, system 200, or both. In particular, system 300 illustrates an example of a ring 305 (e.g., wearable device 104), a user device 310, and a server 315, as described with reference to FIG. 1. Although the system may be implemented by a ring 305, a user device 310, and/or a server 315, any combination of computing devices described herein may implement the features attributed to the system 300. For example, the ring 305 may be an example of a wearable device. The wearable device may include a finger-worn device, a wrist-worn device, a patch, a head-worn device, a chest-worn device, or a combination thereof.

The ring 305 may acquire physiological data 320. The physiological data 320 may include temperature data, heart rate data, respiratory rate data, HRV data, SpO2 data, (e.g., blood oxygen saturation), among other forms of physiological data as described herein. The ring 305 may transmit physiological data 320 to the user device 310, the server 315, or both. The temperature data may include continuous nighttime temperature data. The respiratory rate data may include continuous nighttime breath rate data. In some cases, multiple devices may acquire physiological data 320. The physiological data 320 may be measured from the user for the past day or the past few days (e.g., three days).

In some cases, the ring 305 may acquire baseline data 317, such as baseline PPG data, baseline temperature data, baseline respiratory rate data, baseline heart rate data, baseline HRV data, baseline SpO2 data, and/or other user baseline physiological data. The ring 305 may transmit baseline data 317 to the user device 310 such that the user device and/or the server 315 may receive the baseline data 317 measured from the user via the ring 305. The baseline data 317 may be measured from the user for the few months (e.g., one month, three months, six months, or the like).

The baseline data 317 for the user is periodically updated based on subsequent measurements of the physiological data 320. For example, the baseline data 317 may be adjusted as the time interval changes over time. For example, the baseline data 317 may be calculated from the preceding days, weeks, or months of data from the current calendar day. In such cases, the baseline data 317 may be automatically adjusted as the physiological data 320 is updated based on the time interval changing with the current calendar day.

The baseline data 317 (e.g., temperature, heart rate, respiratory rate, HRV, sleep disturbances, SpO2, and the like) may be tailored specific to the user based on historical data 365 acquired by the system 300. For example, these baselines (e.g., baseline data 317) may represent baseline or average values of physiological parameters or typical trends of physiological values measured prior to measuring the physiological data 320. In some cases, the baselines may differ throughout the period of measurement (e.g., based on the stress, illness, and/or other health-related events) for each physiological parameter. In some cases, the baselines may be based on known standards, averages among users, demographic-specific averages, and the like.

The system 300 may calculate baseline values for the user based on inputting the baseline data 317 into a machine learning model. For example, the baseline data 317 may be calculated based on calculating an average temperature, heart rate, respiratory rate, HRV, SpO2 for a plurality of days (e.g., the past 30 days, the past 90 days, etc.). In some cases, the baseline data 317 may be calculated based on calculating an average value for multiple time periods of the day. For example, the user's temperature may be calculated for each minute, hour, and the like of the calendar day. In some cases, the baseline data 317 may be calculated based on calculating a median value over the plurality of days. The machine learning model may classify the user's baseline data 317 according to average values or median values to determine the user's baseline data 317. In some examples, the system 300 may determine a time series of baseline data 317 values taken over the plurality of months.

In some cases, the system 300 may smooth the baseline data 317, the physiological data 320, or any combination thereof (e.g., using a 7-day smoothing window, a 90-day smoothing window, or other window). The missing values may be imputed (e.g., using the forecaster Impute method from the Python package). In some cases, the ring 305, the user device 310, and/or the servers 315 may be configured to normalize the collected physiological data 320. For example, the ring 305, the user device 310, and/or the servers 315 may be configured to perform one or more normalization procedures on the collected physiological data 320.

In some cases, physiological data 320 (e.g., features of the physiological data 320) may be normalized on a per-night basis. Normalization may account for inter-individual differences in features (e.g., nightly heart rate or HRV). While all parameters/features (e.g., temperature data, accelerometer data, heart rate data, HRV data, PPG data, and the like) may have some discriminatory power to detect different sleep stages, the physiological data 320 may be highly individual, and absolute values may differ greatly between individuals based on parameters other than those of interest (e.g., genetics, age, etc.). In some cases, the components may input the normalized physiological data 320 into a machine learning model.

The system 300 may be configured to perform respective processing procedures described herein using different components of the system 300 in order to reduce a latency of data presented to the user, conserve processing resources, and the like. For example, processing procedures that are more time-sensitive (e.g., lower latency requirements) and/or less computationally expensive (e.g., calculation of Sleep/Readiness Scores) may be performed via the user device 310, whereas processing procedures that are less time-sensitive and/or more computationally expensive (e.g., sleep stage classification procedure) may be performed via the servers 315.

The user device 310 may include the wearable application 330 and an operating system 325. The wearable application 330 may run on the operating system 325 of a user device 310 and may be associated with the ring 305. The wearable application 330 may include LLMs 345, modules 355, and application data 360. The LLMs 345 may include a first messaging tonality 335, additional messaging tonalities 340, messages 350, and additional messages 352.

In some cases, effective guidance (e.g., messages) provided by the system 300 may not be a one-size-fits-all guidance that is universally accepted by all users, and/or that results in improved health outcomes for all users. In other words, users may respond differently to the same tonality used to deliver messages. For example, maintaining a same messaging tone across a wide range of users may discount the user's individual preferences. In order to increase user engagement with the wearable application 330, the ring 305, or both, the system 300 may allow users to adjust the tone of their insights, thereby empowering users to choose the tone of their insight messages and allowing the users to feel more agency over their experience while boosting their levels of engagement. Once the system 300 selects a tone, the tone is infused into the user's insights and notifications, and the tone may be adjusted as described herein.

The system 300 (including the user device 310, the server 315, or both) may generate, using one or more LLMs 345, one or more messages 350 to be provided to the user via the wearable application 330 in response to the baseline physiological data 320 and in accordance with a first messaging tonality 335. After acquiring additional physiological data

320 from the user via the ring 305, the system 300 may perform an evaluation of the first messaging tonality 335 by comparing the additional physiological data 320 with the baseline data 317. In other words, the system 300 may evaluate how well the user responds to the first messaging tonality by evaluating how (or whether) the users physiological data 320 changed relative to the user's baseline data 317. In some cases, the system 300 may select a second messaging tonality from additional messaging tonalities 340 based on the evaluation of the first messaging tonality 335 and generate, using the one or more LLMs 345, one or more additional messages 352 to be provided to the user via the wearable application 330 in accordance with the second messaging tonality.

The first messaging tonality 335 may be changed to an additional messaging tonality 340 based on a trial-and-error testing of tonalities during which the system 300 (including the user device 310, the server 315, or both) may test out different messaging tonalities (e.g., the first messaging tonality 335 and/or additional messaging tonalities 340) for delivering messages 350 and additional messages 352, respectively, to the user. The system 300 may evaluate how the user's actions and/or physiological data 320 responds to the different messaging tonalities, and select which messaging tonality may be used for the user based on how well the user responded to each messaging tonality. In this regard, the wearable application 330 may be configured to provide messages to different users in accordance with different messaging tonalities. That is, some users may respond better to a "drill sergeant" tonality, while other users may respond better to a more empathetic tonality.

In some examples, the first messaging tonality 335 may be changed to an additional messaging tonality 340 based on tailoring the tonality to the user's physiological data 320, the user's baseline data 317, or both. Moreover, the tonality may be tailored or modified based on inputs or preferences received from the user. For example, if the user's physiological data is improving, the system 300 may generate additional messages 352 in accordance with additional messaging tonalities 340 of an upbeat and encouraging tone, for example. In other examples, if the user is unable to reach their goals and/or their health is declining, the system 300 may generate additional messages 352 in accordance with additional messaging tonalities 340 of an empathetic tone, for example. In some cases, the system 300 may change messaging tonalities based on tailoring the tonality to the user's physiological data 320, the user's baseline data 317, or both, and then performing a trial-and-error testing of tonalities in which the system 300 (including the user device 310, the server 315, or both) may test out different messaging tonalities.

The system 300 may personalize a set of characteristics of the messaging tonalities with the user's health outcomes based on the knowledge of the user's baseline data 317, physiological data 320, data trends, and the like. For example, the system 300 may update the messaging tonality used to generate the messages 350 to achieve goals the user has set within the wearable application 330. The set of characteristics may include a word choice, a word arrangement, a punctuation, one or more graphical elements, a volume, a cadence, an inflection, or any combination thereof. In such cases, the first messaging tonality 335 is associated with a first set of characteristics, and wherein the additional messaging tonalities 340 are associated with a second set of characteristics, where the first set of characteristics, the second set of characteristics, or both include the word choice, the word arrangement, the punctuation, one or more graphical elements, the volume, the cadence, the inflection, or any combination thereof.

The tonalities may be an example of a spoken tone, a written tone, or both. In such cases, the user may choose whether to read the messages 350 and/or listen to the messages 350. That is, all users, including users with disabilities, may have options for how they receive their insights in the form of messages 350. In some cases, diverse tones may be delivered in different languages.

The first messaging tonality 335 may be an example of a default messaging tonality that includes a neutral, generic, and objective tone. For example, the message 350 generated in accordance with the first messaging tonality 335 may indicate "If you feel like it today, you should go on a run." In additional or alternative implementations, the user may be able to select the first messaging tonality 335 (e.g., from a list of available tonality options), and/or selected for the user based on the user's responses to a personality test, survey, or questionnaire. In some cases, allowing the user to select the first/original messaging tonality 335 (or selecting the tonality based on the user's determined personality type) may enable the wearable application 250 to utilize the messaging tonality that most closely resembles what the user prefers, or is compatible with the user's personality type. However, as will be described in further detail herein, in cases where the first/original messaging tonality 335 does not seem to motivate the user enough (or over-motivates the user resulting in excessive activity), then the system 300 may be configured to evaluate and change the messaging tonality 335 used for the user. That is, the system 300 may change the messaging tonality 335 for the user based on a state of wellbeing or measured physiological parameters for the user (where the system may return to the first messaging tonality 335 if circumstances indicate that the first messaging tonality 335 is best suited for the user).

The message 350 may be displayed to every user whose biometrics fit a certain set of thresholds or criteria (e.g., whether their physiological data 320 satisfies a threshold for receiving the message 350). However, the first messaging tonality 335 may not motivate every use into action. In such cases, selecting an additional messaging tonality 340 to generate additional messages 352 with an alternative, motivating tone may improve the user's health outcomes by encouraging the user to complete the activity. If the system 300 predicts which messaging tonalities the user best responds to, the prediction may be validated by observing how the physiological data 320 responds to the additional messages 352 generated in accordance with the additional messaging tonalities 340.

The system 300 may generate the messages 350 and/or additional messages 352 using the LLMs 345. For example, the messages 350 and/or additional messages 352 may be generated prior to measuring and/or acquiring the physiological data 320 (e.g., in advance). In such cases, the system 300 may verify the messages 350 and/or additional messages 352 prior to transmitting them to the user. In other examples, the messages 350 and/or additional messages 352 may be generated after measuring and/or acquiring the physiological data 320 (e.g., messages generated in real or near-real time). For example, the system 300 may transmit the messages 350 and/or additional messages 352 based on the collected physiological data 320 without verifying or "spot-checking" the messages, which may result in increased speed and efficiency of the system 300.

The wearable application 330 may include at least modules 355 and application data 360. In some cases, the application data 360 may include historical physiological data patterns for the user and other data. The physiological data patterns may include temperature data, heart rate data, respiratory rate data, HRV data, blood oxygen saturation data, PPG data, or a combination thereof.

The wearable application 330 or the server 315 may adjust the messaging tonalities. The wearable application 330 may present the messages 350 and/or additional messages 352 to the user. The wearable application 330 may include an application data processing module that may perform data processing. For example, the application data processing module may include modules 355 that provide functions attributed to the system 300. Example modules 355 may include a messaging tonality module, a message module, and the like.

In some cases, the user's logged symptoms (e.g., tags) in combination with the user's physiological data 320 and/or baseline data 317 may characterize the messaging tonality. In such cases, the user's logged inputs (e.g., tags) may contribute to adjusting the messaging tonality. In other words, the system 300 may take inputs or tags received from the user into account when selecting the messaging tonality for the user. The logged user inputs may be an example of information associated with a health record of the user (e.g., previous surgeries, pregnancies, illnesses, medications, and the like).

The system 300 may cause a GUI of the user device 310 to display and/or provide an audio output of the messages 350 and the additional messages 352. The system 300 may generate a message 350 for display on a GUI on the user device 310 and/or for audio output by the user device 310. In such cases, the messages 350 may be a written message, an audio message, or both.

In some implementations, the wearable application 330 may notify the user of the messaging tonality and/or prompt the user to perform a variety of tasks in the activity GUI. The notifications and prompts may include text, graphics, and/or other user interface elements. In some cases, the wearable application 330 may display notifications and prompts when there is a change in the messaging tonality. The user device 310 may display notifications and prompts in a separate window on the home screen and/or overlaid onto other screens (e.g., at the very top of the home screen). In some cases, the user device 310 may display the notifications and prompts on a mobile device, a user's watch device, or both.

In some implementations, the user device 310 may store historical data 365. The historical data 365 may include historical temperature patterns of the user, historical heart rate patterns of the user, historical respiratory rate patterns of the user, historical HRV patterns of the user, historical sleep data, historical blood oxygen saturation of the user, or a combination thereof. The historical data 365 may be selected from the last few months. The historical data 365 may be used (e.g., by the user device 310 or server 315) to select the messaging tonality. For example, the system 300 may evaluate the historical data 365 to determine how the user's actions and/or physiological data 320 have changed in the past in response to different messaging tonalities. Using the historical data 365 may allow the user device 310 and/or server 315 to personalize the GUI by taking into consideration the user's historical data 365. In some cases, the historical data 365 may be an example of the baseline data 317.

The user device 310 may transmit historical data 365 to the server 315. In some cases, the transmitted historical data 365 may be the same historical data stored in the wearable application 330. In other examples, the historical data 365 may be different than the historical data stored in the wearable application 330. The server 315 may receive the historical data 365. The server 315 may store the historical data 365 in server data 370.

In some implementations, the user device 310 and/or server 315 may also store other data that may be an example of user information. The user information may include, but is not limited to, user age, weight, height, body mass index, gender, and medical history of the user. In some implementations, the user information may be used as features for adjusting the messaging tonality. The server data 370 may include the other data such as user information.

Figure 4:
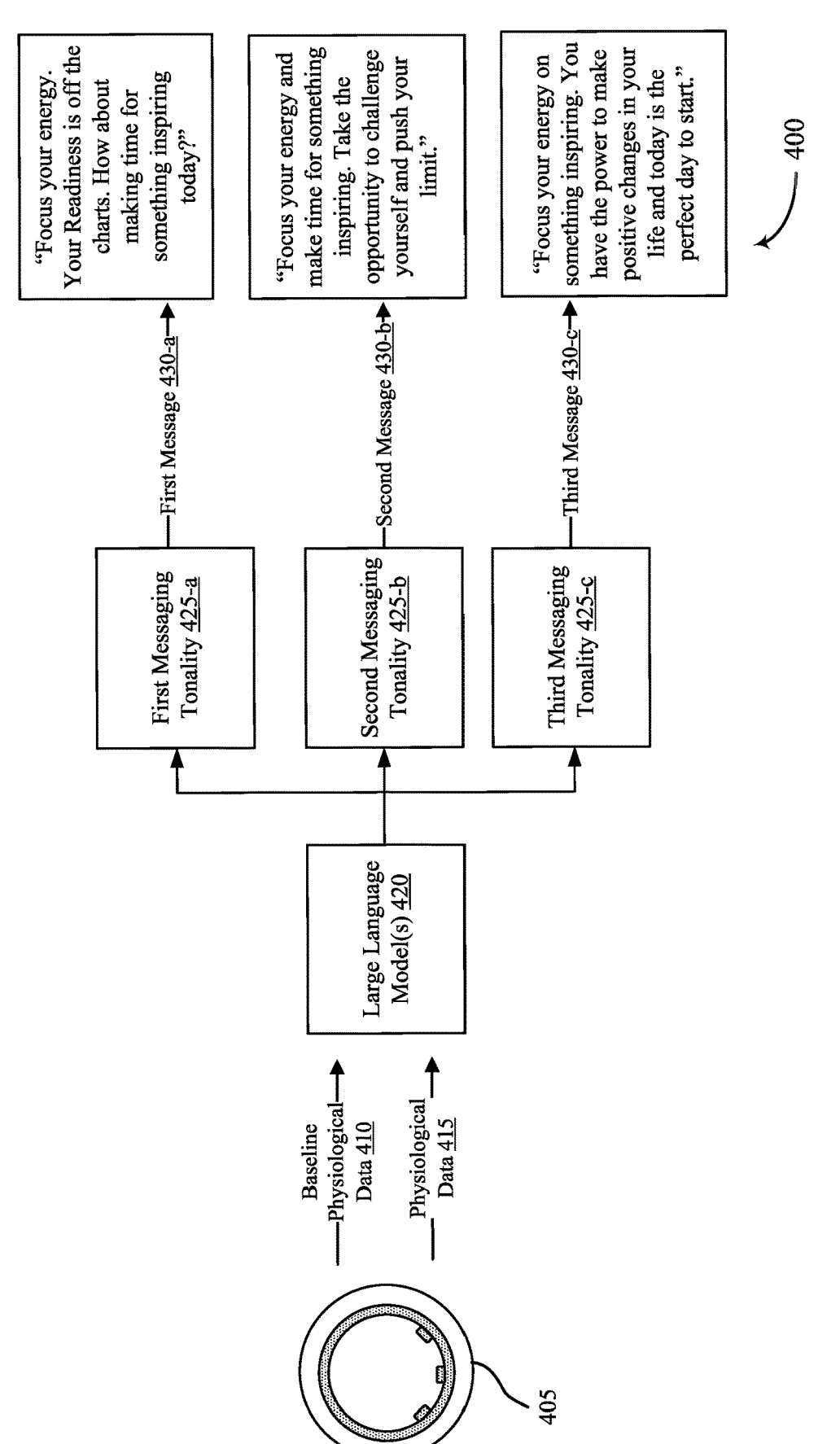
FIG. 4 shows an example of a system that supports techniques for an application tonality adjustment model in accordance with aspects of the present disclosure.

FIG. 4 shows an example of a system 400 that supports techniques for an application tonality adjustment model in accordance with aspects of the present disclosure. The system 400 may implement, or be implemented by, system 100, system 200, system 300, or a combination thereof. In particular, system 400 illustrates an example of a ring 405 (e.g., wearable device 104), an LLM 420, messaging tonalities 425, and messages 430 as described with reference to FIGS. 1 through 3.

The system 400 (e.g., including at least the LLMs 420) may receive baseline physiological data 410 and the physiological data 415 measured from the user by the ring 405. For example, the ring 405 may measure the baseline physiological data 410 from the user, and input the baseline physiological data 410 into the LLMs 420 using one or more processors communicatively coupled with the ring 405 (and/or other devices of the system, such as a user device 106, servers 110, etc.).

The LLMs 420 may include any machine learning classifier or algorithm known in the art including, but not limited to, a Random Forest classifier, a Naïve Bayes classifier, a deep learning classifier, an artificial neural network, and the like. In some cases, machine learning model training and testing may be performed using a Light Gradient Boosting-Machine (LightGBM) classifier, with DART boosting and estimators. LightGBM may provide high accuracy, fast training, low memory usage, and may be capable of handling missing values when data quality is too poor to calculate features. Moreover, the LLMs 420 may be implemented by the ring 405, a user device 106, a server 110, or any combination thereof. In some cases, the LLMs 420 may be trained on the user's physiological data 414, the baseline physiological data 410, or both.

As part of a messaging tonality selection procedure, the messages 430 may be generated using LLMs 420. For example, the messages 430 may be generated in response to inputting the baseline physiological data 410 into the one or more language models 420, inputting the physiological data 415 into the one or more LLMs 420, or both. In some cases, the system 400 may generate a first message 430-a in accordance with a first messaging tonality 425-a based on receiving the baseline physiological data 410. In such cases, the first messaging tonality 425-a may be an example of a default messaging tonality. The first message 430-a may indicate "Focus your energy. Your Readiness is off the charts. How about making time for something inspiring today?"

The system 400 may perform an evaluation of the first messaging tonality 425-a by comparing the additional physiological data 415 with the baseline physiological data 410. For example, the system 400 may determine that the additional physiological data 415 satisfies one or more thresholds based on comparing the additional physiological data 415 with the baseline physiological data 410. In one example, the system 400 may determine that the user's temperature data satisfies (e.g., exceeds) a threshold and, in response, the system 400 may select a messaging tonality 425 from a plurality of messaging tonalities 425.

In some cases, the system 400 may identify a trigger condition to transition from the first messaging tonality 425-*a* to an additional messaging tonality (e.g., the second messaging tonality 425-*b*, the third messaging tonality 425-*c*, and the like) based on acquiring the additional physiological data 415. The selection of an additional messaging tonality (e.g., the second messaging tonality 435-*b*, the third messaging tonality 425-*c*, and the like) is based on identifying the trigger condition. In such cases, the system 400 may switch between tonalities without user interaction. For example, if a user's Sleep Score decreases and the system 400 determines that the user responds well (e.g., the user's physiological data improves) with the third messaging tonality 435-*c*, the system 400 may select the third messaging tonality 425-*c* to generate a third message 430-*c* to change the user's sleep routine and improve the user's Sleep Score.

The system 400 may select which messaging tonality 425 should be used for the user based on how well the user responded to each messaging tonality 425 (e.g., based on how/whether the user's actions and/or physiological data change in response to messages 430 delivered in accordance with the respective messaging tonalities 425). For example, the system 400 may evaluate the new tonality and either keep using the same tonality or switch to a different tonality. In some examples, the system 400 may acquire second physiological data from the user via the wearable device after providing the one or more messages 430 (e.g., second message 430-*b*) to the user in accordance with the second messaging tonality 425-*b*. The second message 430-*b* may indicate "Focus your energy and make time for something inspiring. Take the opportunity to challenge yourself and push your limit."

The system 400 may perform an evaluation of the second messaging tonality 425-*b* by comparing the second physiological data with the baseline physiological data 410, the additional physiological data 415, or both. The system 400 may select the second messaging tonality 425-*b*, the third messaging tonality 425-*c*, or the first messaging tonality 425-*a* from the plurality of messaging tonalities based on the evaluation of the second messaging tonality 425-*b*. The system 400 may generate, using the one or more LLMs 420, one or more additional messages to be provided to the user via the application in accordance with the second messaging tonality 425-*b* or the third messaging tonality 435-*c* based on the selecting.

In some cases, the user may select from the application which type of messaging tonality 425 and/or personality associated with the messaging tonality the user would like to utilize in the application. For example, the user may select a second messaging tonality 425-*b* for personalized coaching. For example, the user may indicate "I want to receive my guidance with a strictness level of 3/5 and empathy level being 0/5." The system 400 may include ready-made persona types including at least a fitness trainer, a professor, a doctor, a celebrity, and the like.

In some cases, the messaging tonalities 425 may be adjusted based on a scale of formal to casual and/or empathetic to rational. In such cases, messages 430 delivered in accordance with different tonalities may include the same general insight or information, but may be conveyed through different word choice, tone, volume, cadence, and the like. For example, multiple messages 430 associated with different tonalities may be delivered to users with an above average Readiness Score and focusing the energy of the user. The first message 430-*a* generated in accordance with the first tonality may indicate "Focus your energy. Your Readiness is off the charts. How about making time for something inspiring today?" The second message 430-*b* generated in accordance with the second tonality may indicate "Focus your energy and make time for something inspiring. Take the opportunity to challenge yourself and push your limit." The third message 430-*c* generated in accordance with the third tonality may indicate "Focus your energy on something inspiring. You have the power to make positive changes in your life and today is the perfect day to start." In this regard, it may be seen that the general insight or information of each message 430-*a*, 430-*b*, 430-*c* is the same, where the only thing that changes is the tonality in which the messages 430 are delivered.

In some cases, the system 400 may personalize the tone of voice of the messages 430 and identify whether the respective messaging tonalities 425 maintain, increase, or decrease a certain health outcome and/or activity for the user. The system 400 may identify that the first messaging tonality 425-*a* increases a health outcome of the user and, in response, the system 400 may generate the first message 430-*a* based on identifying that the first messaging tonality 425-*a* increases a health outcome. In some cases, the system 400 may identify that the second messaging tonality 425-*b* increases an activity level of the user to achieve their activity goal. In such cases, the system 400 may generate the second message 430-*b* based on identifying that the second messaging tonality 425-*b* increases an activity level of the user to achieve their activity goal. In some cases, the system 400 may identify that the third messaging tonality 425-*c* maintains the user's "optimal" Readiness Score, and the system 400 may generate the third message 430-*c* accordingly.

The system 400 may identify which messaging tonality 425 to use to generate the messages 430 based on comparing the physiological data 415 received after providing the message 430 to the user with the selected tonality with the physiological data 415 received before providing the message 430 the user with the selected tonality. In some examples, the system 400 may switch from a first messaging tonality 425-*a* to a second messaging tonality 425-*b* or a third messaging tonality 425-*c* based on determining that the user's physiological data 415 is below a threshold. In such cases, the system 400 may switch to utilize a second messaging tonality 425-*b* and compare the physiological data 415 received after switching to the second messaging tonality 425-*b* and the physiological data 415 acquired when using the first messaging tonality 425-*a*. If the user's physiological data 415 improves, the system 400 may determine to continue using the second messaging tonality 425-*b* to provide the second messages 430-*b* to the user. If the user's physiological data 415 is the same or declines, the system 400 may determine to switch to the third messaging tonality 425-*c* to provide the third message 430-*c* to the user.

The system 400 may generate messages 430 in accordance with the respective messaging tonalities 425 in advance and/or in real or near-real time. For example, upon collecting the physiological data 415, the system may analyze the physiological data 415 and generate the messages 430 in real or near-real time in an automated process. For instance, the system 400 may input one or more evaluations of the baseline physiological data 410 that are output from the one or more machine learning models into the one or more LLMs 420, such that the one or more LLMs 420 generate the messages 430 in accordance with the selected messaging tonality 425 based on the evaluations of the physiological data output by the machine learning models. In such cases, the system 400 may generate the one or more messages based on inputting the one or more evaluations into the one or more LLMs 420.

In other examples, the system 400 may generate messages 430 in accordance with different messaging tonalities in advance (e.g., prior to collecting and/or analyzing the baseline physiological data 410 and/or physiological data 415). For example, the system 400 may generate, using the one or more LLMs 420, the one or more messages 430 that are to be provided to the user in certain scenarios (e.g., when the user's physiological data 410 satisfies certain thresholds or criteria). In such cases, for any physiological data 415 that satisfies certain thresholds, the system 400 has different messages generated for different tonalities. For example, if the user has a certain HRV and heart rate, the system 400 may have different messages (e.g., first message 430-a, second message 430-b, or third message 430-c) that may be delivered with different tonalities.

In such cases, the messages 430 may be generated in advance using LLMs 420 such that the messages 430 are preloaded in advance of receiving the physiological data 415. In such cases, the one or more messages 3430, the one or more additional messages, or both, are generated using the one or more LLMs 420 prior to acquiring the additional physiological data 415 from the user. In some cases, the system 400 may retrieve the one or more messages 430 that are to be provided to the user via the application from a database in response to acquiring the baseline physiological data 410 and/or physiological data 415. For example, the system may determine that the user's activity for the day is lower than usual. In this example, the system may retrieve a message from a database that was generated in accordance with the selected/activated messaging tonality and that is configured to encourage the user to increase their activity.

In some cases, the LLMs 420 may take existing messaging content and output unlimited variations of a message 430 with different messaging tonalities 425. For example, the LLMs 420 may generate a plurality of packets of messages where each packet may include a plurality of variants of the same underlying insight or information. For example, a first packet may include a plurality of variants for a message to improve a Readiness Score. Each variant within the packet may indicate a separate messaging tonality 425 to generate a corresponding message 430 using the messaging tonality 425. That is, the message identification may be the same for each message 430 within the packet. In such cases, the same underlying insight/information may be generated but from different messaging tonalities 425 including at least different tones, personas, archetypes, and the like.

To create the different packets, the system 400 may input the current messaging style (e.g., current messaging tonality 425) into the LLMs 420 to train the LLMs 420 and output the same message 430 using different tonalities. In such cases, the LLMs 420 may generate content that the system 400 may manually validate prior to outputting the message 430 to the user. The system 400 may generate the content (e.g., message) ahead of time prior to receiving the physiological data 415 and then display the message to the user based on receiving the physiological data 415 and determining the physiological data 415 satisfies a threshold.

The system 400 may compare the physiological data and other parameters to the user's baseline physiological data 410 to see if the user's respective scores changed, if the user exercised more, if the user followed the guidance to go to bed earlier, and the like. As such, techniques described herein may provide users with more tailored and actionable guidance to improve their health outcomes as compared to some conventional approaches for generating messages provided to the user.

Figure 5:
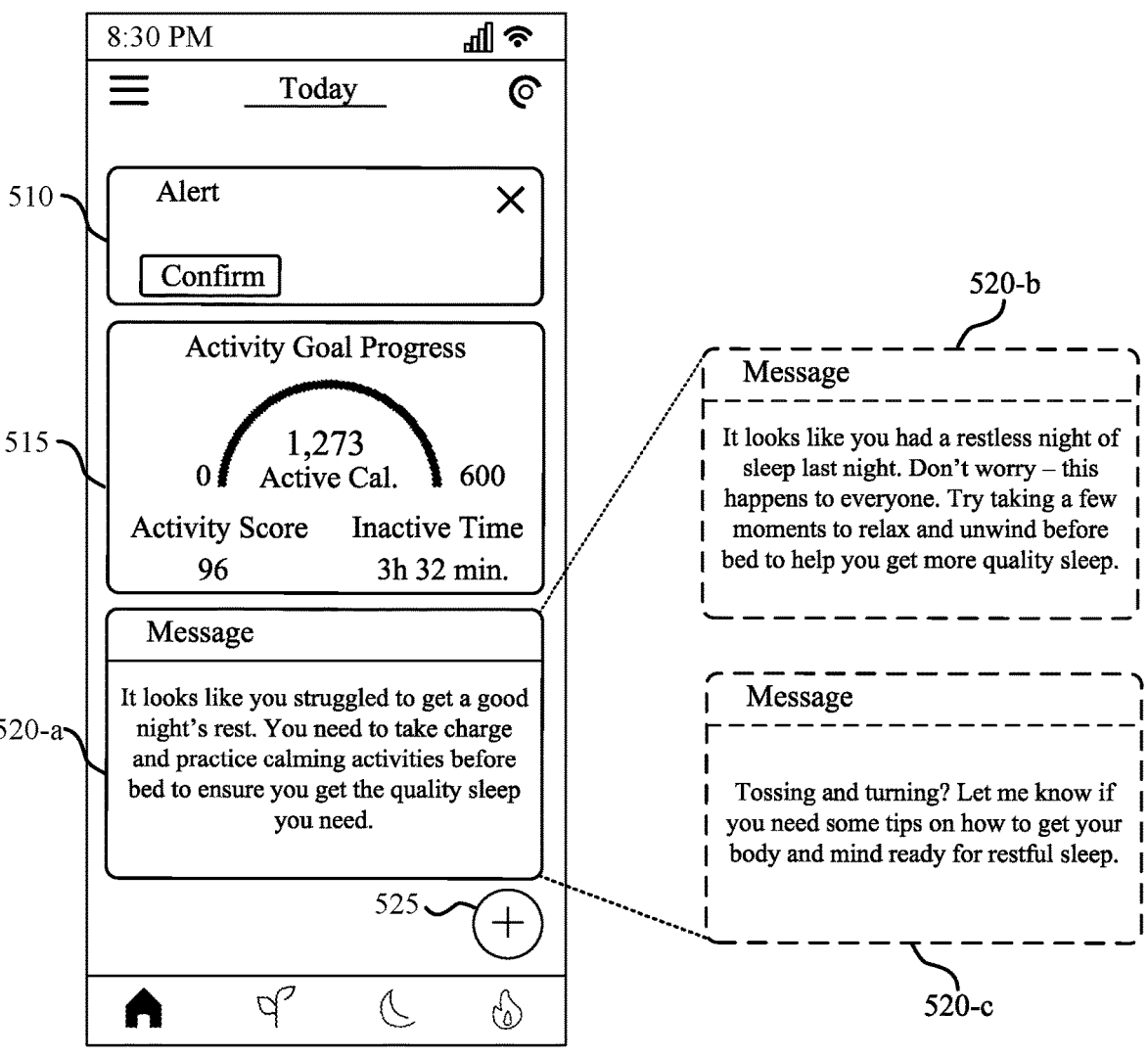
FIG. 5 shows an example of a graphical user interface (GUI) that supports techniques for an application tonality adjustment model in accordance with aspects of the present disclosure.

FIG. 5 shows an example of a GUI 500 that supports techniques for an application tonality adjustment model in accordance with aspects of the present disclosure. The GUI 500 may implement, or be implemented by, aspects of the system 100, system 200, system 300, system 400, or any combination thereof. For example, the GUI 500 may be an example of a GUI 275 of a user device 106 (e.g., user device 106-a, 106-b, 106-c) corresponding to a user 102. In some examples, the GUI 500 illustrates a series of application pages 505 which may be displayed to a user via the GUI 500 (e.g., GUI 275 illustrated in FIG. 2).

The server of the system may generate a message 520 for display on the GUI 500 on a user device. The server of the system may provide an audio output indicating the message 520 generated in accordance with the messaging tonality. For example, the server of system may cause the GUI 500 of the user device (e.g., mobile device) to display a message 520, an alert 510, and/or an information card 515 associated with the user's activity, sleep, Readiness Score, and the like (e.g., via application page 505). In such cases, the system may output the message 520-a generated in accordance with the messaging tonality on the GUI 500 of the user device.

For example, the system may cause the user device to provide a first audio output of the one or more messages 520 in accordance with the first messaging tonality after generating the one or more messages. In other examples, the system may cause the user device to provide a second audio output of the one or more additional messages in accordance with the second messaging tonality after generating the one or more additional messages. In such cases, the system may provide audio (e.g., spoken) messages.

In some cases, the system may cause the GUI 500 of the user device to display the one or more messages 520 in accordance with the first messaging tonality in response to generating the one or more messages. The system may cause the GUI 500 of the user device to display the one or more additional messages in accordance with the second messaging tonality in response to generating the one or more additional messages. In such cases, the system may provide written messages 520 via the GUI 500.

Upon the system selecting the messaging tonality, the user may be presented with the application page 505 upon opening the wearable application. Each time the user is presented with the application page 505 (e.g., opens the application page 505), the system may perform the evaluation, as described herein with reference to FIGS. 3 and 4, to select the messaging tonality. Additionally, or alternatively, once a messaging tonality has been selected, the selected messaging tonality may be used for some amount of time (e.g., a week, a month, etc.) to evaluate whether or not the messaging tonality is effective for the user.

As shown in FIG. 5, the application page 505 may display the message 520, the alert 510 and/or the information card 515. In such cases, the application page 505 may include the message 520, the information card 515, or both, on the home page. In some cases, the information card 515 may not be presented to the user every day upon opening the application page 505 but rather the information card 515 may be included within a trends tab or another feature that shows the information card 515 in the context of longer-term patterns. In cases where the messaging tonality is adjusted, as described herein, the server may transmit an indication (e.g., message 520) to the user, where the message 520 is associated with the messaging tonality.

The messages 520 may be configurable/customizable, such that the user may receive different messages 520 in different tones based on the selected messaging tonality, as described previously herein. For example, based on the messaging tonality, the message 520-a may indicate "It looks like you struggled to get a good night's rest. You need to take charge and practice calming activities before bed to ensure you get the quality sleep you need." Message 520-b may alternatively indicate "It looks like you had a restless night of sleep last night. Don't worry—this happens to everyone. Try taking a few moments to relax and unwind before bed to help you get more quality sleep." Message 520-c may indicate "Tossing and turning? Let me know if you need some tips on how to get your body and mind ready for restful sleep." Each message may convey the same content and/or underlying message, however the tonality of each message may differ.

In such cases, the message 520 may include insights, recommendations, and the like generated in a tone that the best responds to (e.g., results in improved health outcomes). The server of the system may cause the GUI 500 of the user device to display the message 520. For example, the system may transmit, to the user device associated with the wearable device, an instruction to cause the GUI 500 of the user device to display the message 520. As noted previously herein, an accurately selected messaging tonality to generate the messages 520 may be beneficial to a user's overall health.

Additionally, in some implementations, the application page 505 may display one or more scores (e.g., Sleep Score, Readiness Score, Activity Score, etc.) for the user for the respective day. Moreover, in some cases, one or more scores associated with the user (e.g., Sleep Score, Readiness Score, etc.) may be used to update the messaging tonality. That is, data associated with the scores may be used to update the messaging tonality for the following calendar days. In some cases, the system may notify the user of the score update via alert 510. In some cases, the messaging tonality may be adjusted based on the Readiness Score. In such cases, the messaging tonality associated with a Readiness Score that indicates to the user to "pay attention" may be different than a messaging tonality associated with a Readiness Score that indicates to the user "optimal." If the Readiness Score changes for the user, the system may implement a recovery mode for users that may benefit from adjusted activity and readiness guidance for a couple of days, weeks, or months. In such cases, the messaging tonality may be adjusted when a recovery mode for the users is implemented to generate messages 520 with an empathetic tone, for example.

The message 520 may include the insight provided to the user via a written message displayed on the GUI 500, via an audio output provided by the user device, or both. For example, the insight (e.g., message 520) generated with a first messaging tonality may indicate "Your deep sleep is lower than expected. Try taking cold showers before bed to increase your deep sleep and thereby improve your sleep age." In other examples, the insight generated with a second messaging tonality may indicate "You need more deep sleep. Stop looking at your phone before bed and get some rest!" The system may display, via message 520, or provide via audio output, recommendations and/or motivations for healthy habits and provide behavioral insights to the users.

In some cases, the user may log symptoms or events via user input 525. For example, the system may receive user input (e.g., tags) to log symptoms and/or events associated with illness, stress, pregnancy, or the like. For example, the system may receive an indication, via user input 525, of data related to an age of the user, a medical history of the user, one or more tags, a user interaction with the application, user feedback associated with the one or more messages generated in accordance with the first messaging tonality, one or more modifications to the first messaging tonality, or any combination thereof. The medical history of the user may include the indication of illness, stress, pregnancy, alcohol use, exercise history, sleep habits, current medications, previous surgeries, and the like. In other examples, the system may receive the indication of the data related to the health record of the user from the wearable device, physiological data from the wearable device, or both. The physiological data from the wearable device may be an example of temperature, heart rate, HRV, respiratory rate, sleep data, blood pressure, and the like. In some cases, the application page 505 may indicate one or more parameters, including the physiological data, and the like via the information card 515.

In some cases, the system may adjust the messaging tonality in response to receiving the indication. For example, the messaging tonality may be adjusted based on a medical history of the patient, physiological data obtained from the wearable device, or both. The system may cause the GUI 500 to provide the indication verbally and/or display the indication (via alert 510, information card 515, and/or message 520) after selecting the messaging tonality. In such cases, the system may adjust the characteristics of the insights, recommendations, and the like based on the selected messaging tonality. For example, the system may indicate, using a first messaging tonality, "Need a new challenge? Looks like you have been less active than usual. If you feel good, today could be a good day to get moving." In some examples, the system may indicate, using a second messaging tonality, "Regular daily activity will help give you more energy and improve your mood. Try implementing a consistent exercise routine, and the time to start is now!" In some cases, the user may input a tag via user input 525 that indicates the user is sick. In such cases, the messaging tonality may be updated to include an empathetic tone rather than an encouraging and/or motivating tone.

As shown in FIG. 5, the user may receive alert 510, and the application page 505 may prompt the user to confirm or dismiss the alert 510 and/or the adjusted messaging tonality. For example, the system may receive, via a user device and in response to adjusting the messaging tonality, a confirmation of the updated messaging tonality. For example, the user may be able to provide feedback, via user input 525, of whether the user approves (e.g., like) the selected messaging tonality or disapproves (e.g., dislikes) the selected messaging tonality. The user may provide via user input 525 modifications to the selected messaging tonality. For example, the user may provide via the user input 525 that the user would like an increased amount of symbols used in the messages 520 or that the user would like a more encouraging tone. In such cases, the system transitions to different messaging tonalities based on user interaction with the application (e.g., receiving confirmation to change tonalities, user feedback of whether the user like the new tone, etc.)

In some cases, the user may provide, via user input 525, a selection of a messaging tonality from a plurality of messaging tonalities. In such cases, the user may make a subjective choice as to which messaging tonality the messages 520 may be generated with based on a type of coaching and/or instructions they want to receive. For example, the user may toggle between different messaging tonalities based on the user's personal preferences.

In some implementations, the system may provide additional insight regarding the user's selected messaging tonality. For example, the application pages 505 may indicate one or more physiological parameters (e.g., contributing factors) which resulted in the user's selected messaging tonality, such as exercise habits, sleep habits, and the like. In other words, the system may be configured to provide some information or other insights regarding the selected messaging tonality. Personalized insights may indicate aspects of collected physiological data (e.g., contributing factors within the physiological data) which were used to select the messaging tonality.

In some implementations, the system may be configured to receive user inputs 525 regarding the selected messaging tonality in order to train classifiers (e.g., supervised learning for a machine learning classifier, the LLMs, and the like) and improve messaging tonality selection techniques. For example, the user device may receive user inputs 525, and these user inputs 525 may then be input into a machine learning model, LLMs, or both to train the machine learning model. In some cases, the physiological data may be inputted into the machine learning model. In such cases, the system may select the messaging tonality in response to inputting the physiological data into the machine learning model.

In some cases, the messaging tonality may be selected based on a personality type of the user. For example, the user may complete a personality test (e.g., survey, questionnaire, etc.) upon joining the application to determine a personality type. Based on the personality type of the user, the system may select the messaging tonality to generate the messages provided to the user. For example, the system may identify a personality type of the user based on user interactions with the application. In such cases, the messaging tonality may be selected based on identifying the personality type. For example, the system identifies a personality type and selects the messaging tonality based on the personality type (i.e., interactions with the application, how long the user stays on the information card 515, etc.)

In some cases, the personality type of the user may be determined based on a charging pattern of the ring (e.g., how often and/or how long), how often and/or how long the user accesses the application, which features the users accesses within the application and for how long the user accesses. In such cases, the system may determine an initial messaging tonality to provide messages to the user, and may update the tonality that is used to deliver subsequent messages based on the techniques described herein.

Figure 6:
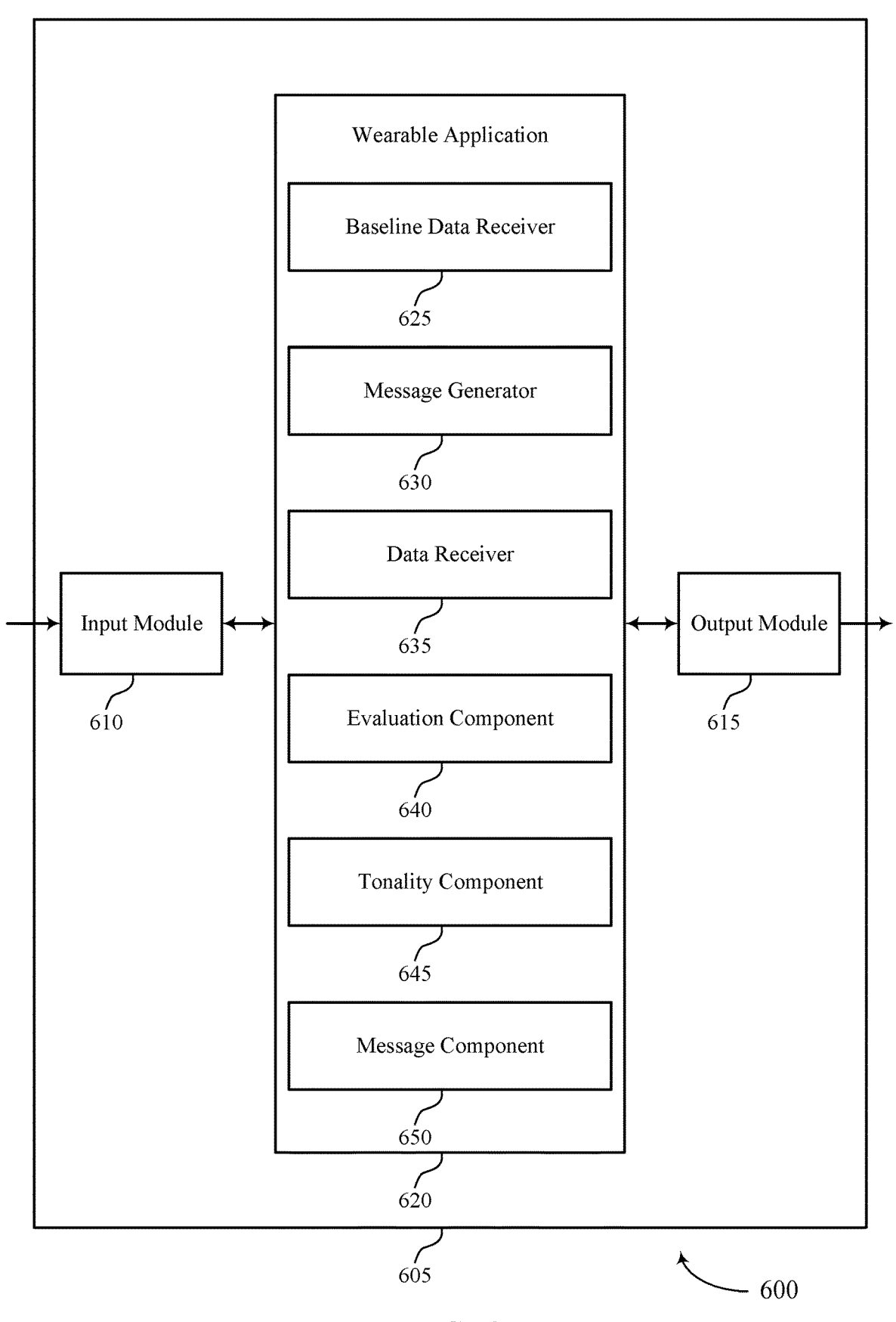
FIG. 6 shows a block diagram of an apparatus that supports techniques for an application tonality adjustment model in accordance with aspects of the present disclosure.

FIG. 6 shows a block diagram 600 of a device 605 that supports techniques for an application tonality adjustment model in accordance with aspects of the present disclosure. The device 605 may include an input module 610, an output module 615, and a wearable application 620. The device 605, or one of more components of the device 605 (e.g., the input module 610, the output module 615, and the wearable application 620), may include at least one processor, which may be coupled with at least one memory, to support the described techniques. Each of these components may be in communication with one another (e.g., via one or more buses).

The input module 610 may provide a means for receiving information such as packets, user data, control information, or any combination thereof associated with various information channels (e.g., control channels, data channels, information channels related to illness detection techniques). Information may be passed on to other components of the device 605. The input module 610 may utilize a single antenna or a set of multiple antennas.

The output module 615 may provide a means for transmitting signals generated by other components of the device 605. For example, the output module 615 may transmit information such as packets, user data, control information, or any combination thereof associated with various information channels (e.g., control channels, data channels, information channels related to illness detection techniques). In some examples, the output module 615 may be co-located with the input module 610 in a transceiver module. The output module 615 may utilize a single antenna or a set of multiple antennas.

For example, the wearable application 620 may include a baseline data receiver 625, a message generator 630, a data receiver 635, an evaluation component 640, a tonality component 645, a message component 650, or any combination thereof. In some examples, the wearable application 620, or various components thereof, may be configured to perform various operations (e.g., receiving, monitoring, transmitting) using or otherwise in cooperation with the input module 610, the output module 615, or both. For example, the wearable application 620 may receive information from the input module 610, send information to the output module 615, or be integrated in combination with the input module 610, the output module 615, or both to receive information, transmit information, or perform various other operations as described herein.

The baseline data receiver 625 may be configured as or otherwise support a means for acquiring baseline physiological data measured from the user via the wearable device. The message generator 630 may be configured as or otherwise support a means for generating, using one or more LLMs, one or more messages to be provided to the user via the application in response to the baseline physiological data and in accordance with a first messaging tonality. The data receiver 635 may be configured as or otherwise support a means for acquiring additional physiological data from the user via the wearable device based at least in part on providing the one or more messages to the user in accordance with the first messaging tonality. The evaluation component 640 may be configured as or otherwise support a means for performing an evaluation of the first messaging tonality by comparing the additional physiological data with the baseline physiological data. The tonality component 645 may be configured as or otherwise support a means for selecting a second messaging tonality from a plurality of messaging tonalities based at least in part on the evaluation of the first messaging tonality, wherein the second messaging tonality is associated with the one or more LLMs. The message component 650 may be configured as or otherwise support a means for generating, using the one or more LLMs, one or more additional messages to be provided to the user via the application in accordance with the second messaging tonality based at least in part on selecting the second messaging tonality.

Figure 7:
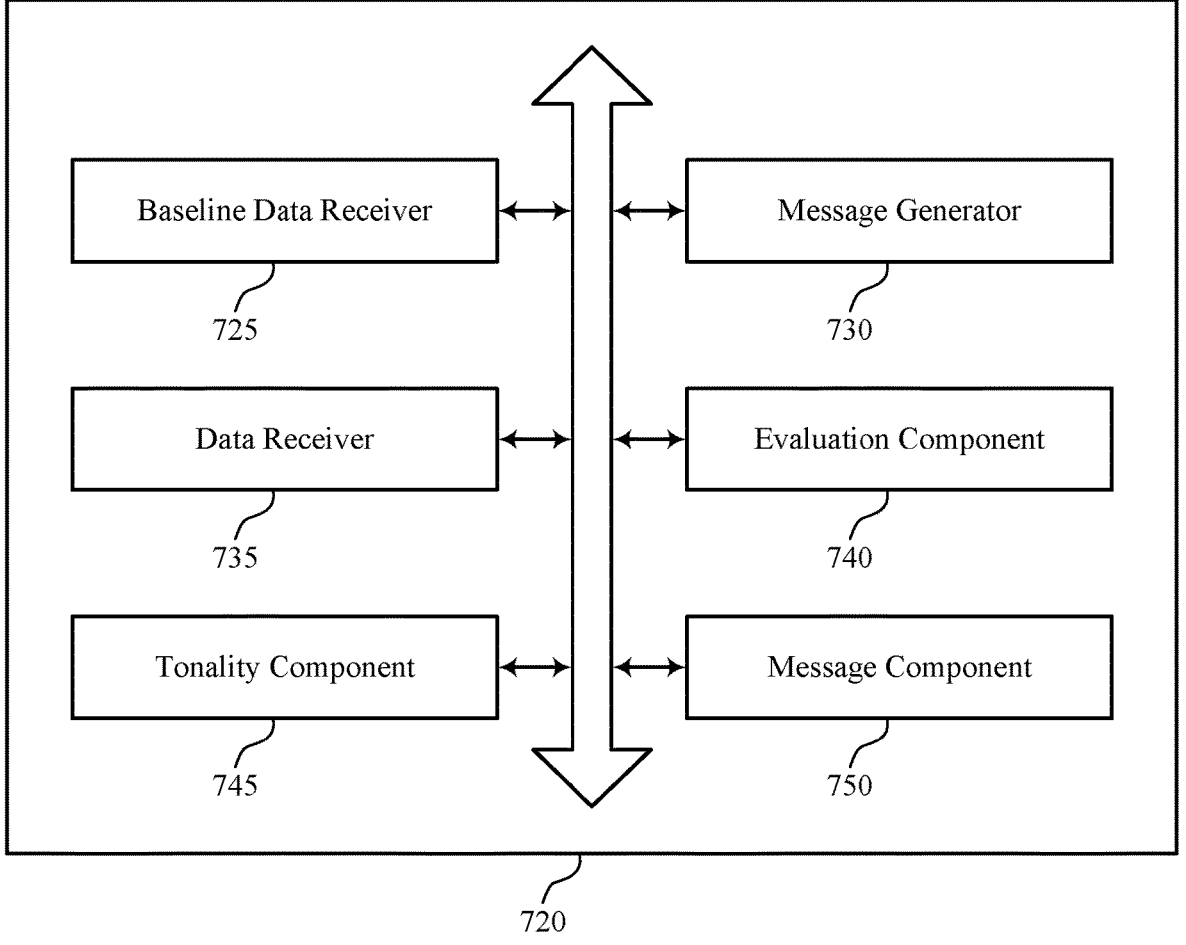
FIG. 7 shows a block diagram of a wearable application that supports techniques for an application tonality adjustment model in accordance with aspects of the present disclosure.

FIG. 7 shows a block diagram 700 of a wearable application 720 that supports techniques for an application tonality adjustment model in accordance with aspects of the present disclosure. The wearable application 720 may be an example of aspects of a wearable application or a wearable application 620, or both, as described herein. The wearable application 720, or various components thereof, may be an example of means for performing various aspects of application tonality adjustment model as described herein. For example, the wearable application 720 may include a baseline data receiver 725, a message generator 730, a data receiver 735, an evaluation component 740, a tonality component 745, a message component 750, or any combination thereof. Each of these components, or components of subcomponents thereof (e.g., one or more processors, one or more memories), may communicate, directly or indirectly, with one another (e.g., via one or more buses).

The baseline data receiver 725 may be configured as or otherwise support a means for acquiring baseline physiological data measured from the user via the wearable device. The message generator 730 may be configured as or otherwise support a means for generating, using one or more LLMs, one or more messages to be provided to the user via the application in response to the baseline physiological data and in accordance with a first messaging tonality. The data receiver 735 may be configured as or otherwise support a means for acquiring additional physiological data from the user via the wearable device based at least in part on providing the one or more messages to the user in accordance with the first messaging tonality. The evaluation component 740 may be configured as or otherwise support a means for performing an evaluation of the first messaging tonality by comparing the additional physiological data with the baseline physiological data. The tonality component 745 may be configured as or otherwise support a means for selecting a second messaging tonality from a plurality of messaging tonalities based at least in part on the evaluation of the first messaging tonality, wherein the second messaging tonality is associated with the one or more LLMs. The message component 750 may be configured as or otherwise support a means for generating, using the one or more LLMs, one or more additional messages to be provided to the user via the application in accordance with the second messaging tonality based at least in part on selecting the second messaging tonality.

In some examples, the data receiver 735 may be configured as or otherwise support a means for acquiring second physiological data from the user via the wearable device based at least in part on providing the one or more messages to the user in accordance with the second messaging tonality. In some examples, the evaluation component 740 may be configured as or otherwise support a means for performing an evaluation of the second messaging tonality by comparing the second physiological data with the baseline physiological data, the additional physiological data, or both. In some examples, the tonality component 745 may be configured as or otherwise support a means for selecting the second messaging tonality or a third messaging tonality from the plurality of messaging tonalities based at least in part on the evaluation of the second messaging tonality. In some examples, the message generator 730 may be configured as or otherwise support a means for generating, using the one or more LLMs, one or more additional messages to be provided to the user via the application in accordance with the second messaging tonality or the third messaging tonality based at least in part on the selecting.

In some examples, the one or more messages, the one or more additional messages, or both, are generated using the one or more LLMs prior to acquiring the additional physiological data from the user. In some examples, the data receiver 735 may be configured as or otherwise support a means for retrieving the one or more messages that are to be provided to the user via the application from a database based at least in part on acquiring the baseline physiological data. In some examples, the message component 750 may be configured as or otherwise support a means for retrieving the one or more additional messages that are to be provided to the user via the application from the database based at least in part on acquiring the additional physiological data.

In some examples, the data receiver 735 may be configured as or otherwise support a means for receiving a physiological data set from the user, one or more additional users, or both. In some examples, the data receiver 735 may be configured as or otherwise support a means for determining that the physiological data set satisfies one or more thresholds. In some examples, the message generator 730 may be configured as or otherwise support a means for generating, using the one or more LLMs, the one or more messages that are to be provided to the user in accordance with the first messaging tonality based at least in part on the baseline physiological data, the additional physiological data, or both, satisfying the one or more thresholds. In some examples, the message generator 730 may be configured as or otherwise support a means for generating, using the one or more LLMs, the one or more additional messages that are to be provided to the user in accordance with the second messaging tonality based at least in part on the baseline physiological data, the additional physiological data, or both, satisfying the one or more thresholds.

In some examples, the baseline data receiver 725 may be configured as or otherwise support a means for inputting baseline physiological data into one or more machine learning models. In some examples, the evaluation component 740 may be configured as or otherwise support a means for inputting one or more evaluations of the baseline physiological data that are output from the one or more machine learning models into the one or more LLMs, wherein generating the one or more messages is based at least in part on inputting the one or more evaluations into the one or more LLMs.

In some examples, the evaluation component 740 may be configured as or otherwise support a means for identifying a personality type of the user based at least in part on user interactions with the application, wherein selecting the second messaging tonality is based at least in part on identifying the personality type.

In some examples, the data receiver 735 may be configured as or otherwise support a means for determining that the additional physiological data satisfies one or more thresholds based at least in part on comparing the additional physiological data with the baseline physiological data, wherein the second messaging tonality is selected from the plurality of messaging tonalities based at least in part on determining the additional physiological data satisfies the one or more thresholds.

In some examples, the tonality component 745 may be configured as or otherwise support a means for identifying a trigger condition to transition from the first messaging tonality to the second messaging tonality based at least in part on acquiring the additional physiological data, wherein selecting the second messaging tonality is based at least in part on identifying the trigger condition.

In some examples, the data receiver 735 may be configured as or otherwise support a means for receiving a user input comprising an age of the user, a medical history of the user, one or more tags, a user interaction with the application, user feedback associated with the one or more messages generated in accordance with the first messaging tonality, one or more modifications to the first messaging tonality, or any combination thereof, wherein selecting the second messaging tonality is based at least in part on receiving the user input.

In some examples, the message component 750 may be configured as or otherwise support a means for causing a GUI of the user device to display the one or more messages in accordance with the first messaging tonality based at least in part on generating the one or more messages. In some examples, the message component 750 may be configured as or otherwise support a means for causing the GUI of the user device to display the one or more additional messages in accordance with the second messaging tonality based at least in part on generating the one or more additional messages.

In some examples, the message component 750 may be configured as or otherwise support a means for causing the user device to provide a first audio output of the one or more messages in accordance with the first messaging tonality based at least in part on generating the one or more messages. In some examples, the message component 750 may be configured as or otherwise support a means for causing the user device to provide a second audio output of the one or more additional messages in accordance with the second messaging tonality based at least in part on generating the one or more additional messages.

In some examples, the baseline data receiver 725 may be configured as or otherwise support a means for inputting the baseline physiological data into the one or more LLMs based at least in part on receiving the baseline physiological data, wherein generating the one or more messages are based at least in part on inputting the baseline physiological data into the one or more LLMs. In some examples, the data receiver 735 may be configured as or otherwise support a means for inputting the additional physiological data into the one or more LLMs based at least in part on acquiring the additional physiological data, wherein generating the one or more additional messages are based at least in part on inputting the additional physiological data into the one or more LLMs.

In some examples, the first messaging tonality is associated with a first set of characteristics. In some examples, the second messaging tonality is associated with a second set of characteristics. In some examples, the first set of characteristics, the second set of characteristics, or both, comprise a word choice, a word arrangement, a punctuation, one or more graphical elements, a volume, a cadence, an inflection, or any combination thereof.

In some examples, the wearable device comprises a finger-worn device, a wrist-worn device, a patch, a head-worn device, a chest-worn device, or a combination thereof.

In some examples, the one or more processors are located within the wearable device, within the user device, with a server, or any combination thereof.

In some examples, the wearable device collects the baseline physiological data and the additional physiological data from the user based on arterial blood flow, capillary blood flow, arteriole blood flow, or a combination thereof.

Figure 8:
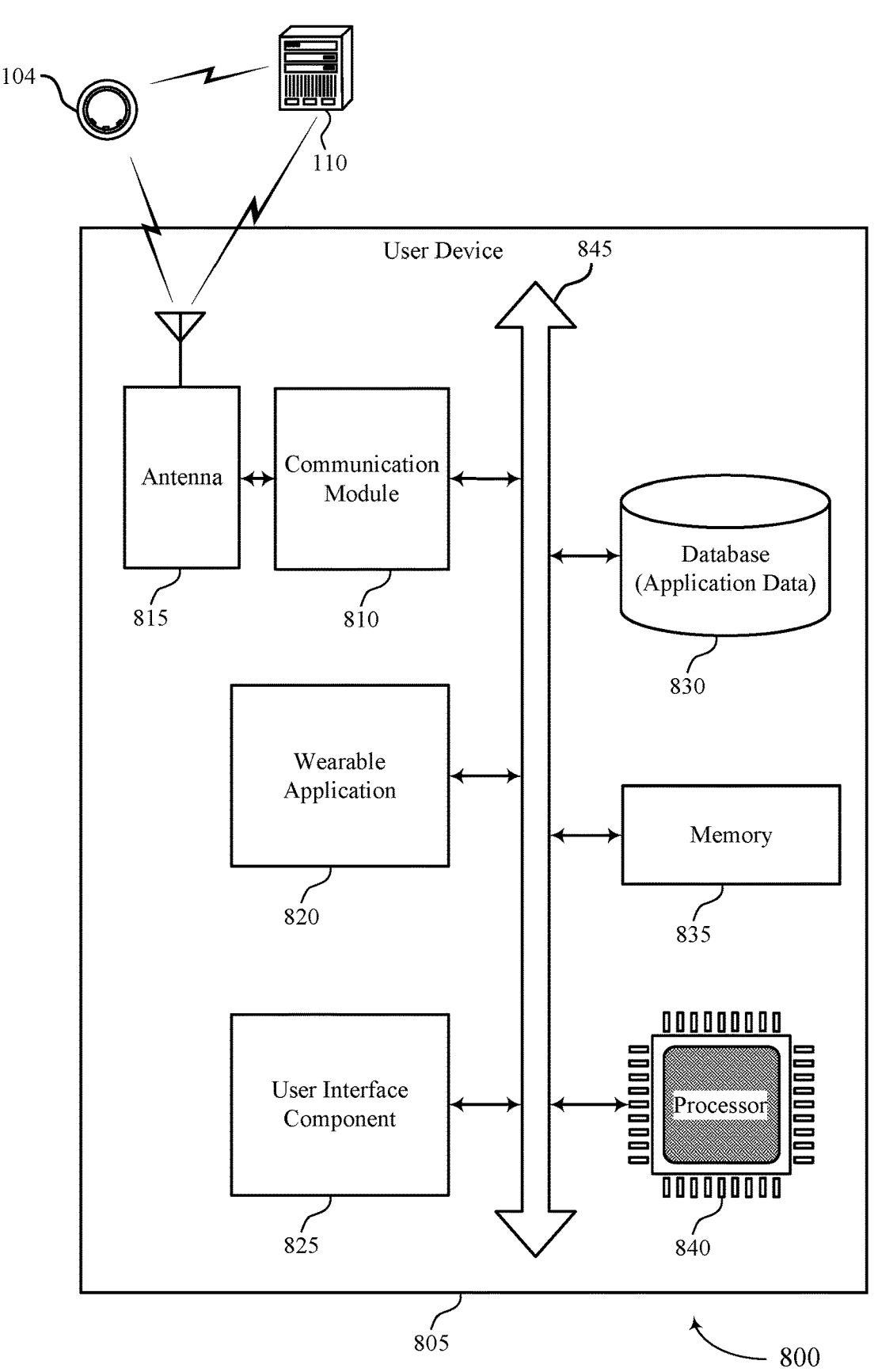
FIG. 8 shows a diagram of a system including a device that supports techniques for an application tonality adjustment model in accordance with aspects of the present disclosure.

FIG. 8 shows a diagram of a system 800 including a device 805 that supports techniques for an application tonality adjustment model in accordance with aspects of the present disclosure. The device 805 may be an example of or include the components of a device 605 as described herein. The device 805 may include an example of a user device 106, as described previously herein. The device 805 may include components for bi-directional communications including components for transmitting and receiving communications with a wearable device 104 and a server 110, such as a wearable application 820, a communication module 810, an antenna 815, a user interface component 825, a database (application data) 830, at least one memory 835, and at least one processor 840. These components may be in electronic communication or otherwise coupled (e.g., operatively, communicatively, functionally, electronically, electrically) via one or more buses (e.g., a bus 845).

The communication module 810 may manage input and output signals for the device 805 via the antenna 815. The communication module 810 may include an example of the communication module 220-b of the user device 106 shown and described in FIG. 2. In this regard, the communication module 810 may manage communications with the ring 104 and the server 110, as illustrated in FIG. 2. The communication module 810 may also manage peripherals not integrated into the device 805. In some cases, the communication module 810 may represent a physical connection or port to an external peripheral. In some cases, the communication module 810 may utilize an operating system such as iOS®, ANDROID®, MS-DOS®, MS-WINDOWS®, OS/2®, UNIX®, LINUX®, or another known operating system. In other cases, the communication module 810 may represent or interact with a wearable device (e.g., ring 104), modem, a keyboard, a mouse, a touchscreen, or a similar device. In some cases, the communication module 810 may be implemented as part of the processor 840. In some examples, a user may interact with the device 805 via the communication module 810, user interface component 825, or via hardware components controlled by the communication module 810.

In some cases, the device 805 may include a single antenna 815. However, in some other cases, the device 805 may have more than one antenna 815, which may be capable of concurrently transmitting or receiving multiple wireless transmissions. The communication module 810 may communicate bi-directionally, via the one or more antennas 815, wired, or wireless links as described herein. For example, the communication module 810 may represent a wireless transceiver and may communicate bi-directionally with another wireless transceiver. The communication module 810 may also include a modem to modulate the packets, to provide the modulated packets to one or more antennas 815 for transmission, and to demodulate packets received from the one or more antennas 815.

The user interface component 825 may manage data storage and processing in a database 830. In some cases, a user may interact with the user interface component 825. In other cases, the user interface component 825 may operate automatically without user interaction. The database 830 may be an example of a single database, a distributed database, multiple distributed databases, a data store, a data lake, or an emergency backup database.

The memory 835 may include RAM and ROM. The memory 835 may store computer-readable, computer-executable software including instructions that, when executed, cause the processor 840 to perform various functions described herein. In some cases, the memory 835 may contain, among other things, a BIOS which may control basic hardware or software operation such as the interaction with peripheral components or devices.

The processor 840 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 840 may be configured to operate a memory array using a memory controller. In other cases, a memory controller may be integrated into the processor 840. The processor 840 may be configured to execute computer-readable instructions stored in a memory 835 to perform various functions (e.g., functions or tasks supporting a method and system for sleep staging algorithms).

For example, the wearable application 820 may be configured as or otherwise support a means for acquiring baseline physiological data measured from the user via the wearable device. The wearable application 820 may be configured as or otherwise support a means for generating, using one or more LLMs, one or more messages to be provided to the user via the application in response to the baseline physiological data and in accordance with a first messaging tonality. The wearable application 820 may be configured as or otherwise support a means for acquiring additional physiological data from the user via the wearable device based at least in part on providing the one or more messages to the user in accordance with the first messaging tonality. The wearable application 820 may be configured as or otherwise support a means for performing an evaluation of the first messaging tonality by comparing the additional physiological data with the baseline physiological data. The wearable application 820 may be configured as or otherwise support a means for selecting a second messaging tonality from a plurality of messaging tonalities based at least in part on the evaluation of the first messaging tonality, wherein the second messaging tonality is associated with the one or more LLMs. The wearable application 820 may be configured as or otherwise support a means for generating, using the one or more LLMs, one or more additional messages to be provided to the user via the application in accordance with the second messaging tonality based at least in part on selecting the second messaging tonality.

By including or configuring the wearable application 820 in accordance with examples as described herein, the device 805 may support techniques for improved communication reliability, reduced latency, improved user experience related to reduced processing, reduced power consumption, more efficient utilization of communication resources, improved coordination between devices, longer battery life, improved utilization of processing capability.

The wearable application 820 may include an application (e.g., "app"), program, software, or other component which is configured to facilitate communications with a ring 104, server 110, other user devices 106, and the like. For example, the wearable application 820 may include an application executable on a user device 106 which is configured to receive data (e.g., physiological data) from a ring 104, perform processing operations on the received data, transmit and receive data with the servers 110, and cause presentation of data to a user 102.

FIG. 9 shows a flowchart illustrating a method 900 that supports techniques for an application tonality adjustment model in accordance with aspects of the present disclosure. The operations of the method 900 may be implemented by a user device or its components as described herein. For example, the operations of the method 900 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 905, the method may include acquiring baseline physiological data measured from the user via the wearable device. The operations of block 905 may be performed in accordance with examples as disclosed herein. In some examples, aspects of the operations of 905 may be performed by a baseline data receiver 725 as described with reference to FIG. 7.

At 910, the method may include generating, using one or more LLMs, one or more messages to be provided to the user via the application in response to the baseline physiological data and in accordance with a first messaging tonality. The operations of block 910 may be performed in accordance with examples as disclosed herein. In some examples, aspects of the operations of 910 may be performed by a message generator 730 as described with reference to FIG. 7.

At 915, the method may include acquiring additional physiological data from the user via the wearable device based at least in part on providing the one or more messages to the user in accordance with the first messaging tonality. The operations of block 915 may be performed in accordance with examples as disclosed herein. In some examples, aspects of the operations of 915 may be performed by a data receiver 735 as described with reference to FIG. 7.

At 920, the method may include performing an evaluation of the first messaging tonality by comparing the additional physiological data with the baseline physiological data. The operations of block 920 may be performed in accordance with examples as disclosed herein. In some examples, aspects of the operations of 920 may be performed by an evaluation component 740 as described with reference to FIG. 7.

At 925, the method may include selecting a second messaging tonality from a plurality of messaging tonalities based at least in part on the evaluation of the first messaging tonality, wherein the second messaging tonality is associated with the one or more LLMs. The operations of block 925 may be performed in accordance with examples as disclosed herein. In some examples, aspects of the operations of 925 may be performed by a tonality component 745 as described with reference to FIG. 7.

At 930, the method may include generating, using the one or more LLMs, one or more additional messages to be provided to the user via the application in accordance with the second messaging tonality based at least in part on selecting the second messaging tonality. The operations of block 930 may be performed in accordance with examples as disclosed herein. In some examples, aspects of the operations of 930 may be performed by a message component 750 as described with reference to FIG. 7.

It should be noted that the methods described above describe possible implementations, and that the operations and the steps may be rearranged or otherwise modified and that other implementations are possible. Furthermore, aspects from two or more of the methods may be combined.

A method is described. The method may include acquiring baseline physiological data measured from the user via the wearable device, generating, using one or more LLMs, one or more messages to be provided to the user via the application in response to the baseline physiological data and in accordance with a first messaging tonality, acquiring additional physiological data from the user via the wearable device based at least in part on providing the one or more messages to the user in accordance with the first messaging tonality, performing an evaluation of the first messaging tonality by comparing the additional physiological data with the baseline physiological data, selecting a second messaging tonality from a plurality of messaging tonalities based at least in part on the evaluation of the first messaging tonality, wherein the second messaging tonality is associated with the one or more LLMs, and generating, using the one or more LLMs, one or more additional messages to be provided to the user via the application in accordance with the second messaging tonality based at least in part on selecting the second messaging tonality.

An apparatus is described. The apparatus may include one or more memories storing processor executable code, and one or more processors coupled with the one or more memories. The one or more processors may individually or collectively operable to execute the code to cause the apparatus to acquire baseline physiological data measured from the user via the wearable device, generate, using one or more LLMs, one or more messages to be provided to the user via the application in response to the baseline physiological data and in accordance with a first messaging tonality, acquire additional physiological data from the user via the wearable device based at least in part on providing the one or more messages to the user in accordance with the first messaging tonality, perform an evaluation of the first messaging tonality by comparing the additional physiological data with the baseline physiological data, select a second messaging tonality from a plurality of messaging tonalities based at least in part on the evaluation of the first messaging tonality, wherein the second messaging tonality is associated with the one or more LLMs, and generate, using the one or more LLMs, one or more additional messages to be provided to the user via the application in accordance with the second messaging tonality based at least in part on selecting the second messaging tonality.

Another apparatus is described. The apparatus may include means for acquiring baseline physiological data measured from the user via the wearable device, means for generating, using one or more LLMs, one or more messages to be provided to the user via the application in response to the baseline physiological data and in accordance with a first messaging tonality, means for acquiring additional physiological data from the user via the wearable device based at least in part on providing the one or more messages to the user in accordance with the first messaging tonality, means for performing an evaluation of the first messaging tonality by comparing the additional physiological data with the baseline physiological data, means for selecting a second messaging tonality from a plurality of messaging tonalities based at least in part on the evaluation of the first messaging tonality, wherein the second messaging tonality is associated with the one or more LLMs, and means for generating, using the one or more LLMs, one or more additional messages to be provided to the user via the application in accordance with the second messaging tonality based at least in part on selecting the second messaging tonality.

A non-transitory computer-readable medium storing code is described. The code may include instructions executable by a processor to acquire baseline physiological data measured from the user via the wearable device, generate, using one or more LLMs, one or more messages to be provided to the user via the application in response to the baseline physiological data and in accordance with a first messaging tonality, acquire additional physiological data from the user via the wearable device based at least in part on providing the one or more messages to the user in accordance with the first messaging tonality, perform an evaluation of the first messaging tonality by comparing the additional physiological data with the baseline physiological data, select a second messaging tonality from a plurality of messaging tonalities based at least in part on the evaluation of the first messaging tonality, wherein the second messaging tonality is associated with the one or more LLMs, and generate, using the one or more LLMs, one or more additional messages to be provided to the user via the application in accordance with the second messaging tonality based at least in part on selecting the second messaging tonality.

Some examples of the method, apparatus, and non-transitory computer-readable medium described herein may further include operations, features, means, or instructions for acquiring second physiological data from the user via the wearable device based at least in part on providing the one or more messages to the user in accordance with the second messaging tonality, performing an evaluation of the second messaging tonality by comparing the second physiological data with the baseline physiological data, the additional physiological data, or both, selecting the second messaging tonality or a third messaging tonality from the plurality of messaging tonalities based at least in part on the evaluation of the second messaging tonality, and generating, using the one or more LLMs, one or more additional messages to be provided to the user via the application in accordance with the second messaging tonality or the third messaging tonality based at least in part on the selecting.

Some examples of the method, apparatus, and non-transitory computer-readable medium described herein may further include operations, features, means, or instructions for retrieving the one or more messages that may be to be provided to the user via the application from a database based at least in part on acquiring the baseline physiological data and retrieving the one or more additional messages that may be to be provided to the user via the application from the database based at least in part on acquiring the additional physiological data.

Some examples of the method, apparatus, and non-transitory computer-readable medium described herein may further include operations, features, means, or instructions for receiving a physiological data set from the user, one or more additional users, or both, determining that the physiological data set satisfies one or more thresholds, generating, using the one or more LLMs, the one or more messages that may be to be provided to the user in accordance with the first messaging tonality based at least in part on the baseline physiological data, the additional physiological data, or both, satisfying the one or more thresholds, and generating, using the one or more LLMs, the one or more additional messages that may be to be provided to the user in accordance with the second messaging tonality based at least in part on the baseline physiological data, the additional physiological data, or both, satisfying the one or more thresholds.

Some examples of the method, apparatus, and non-transitory computer-readable medium described herein may further include operations, features, means, or instructions for inputting the baseline physiological data into one or more machine learning models and inputting one or more evaluations of the baseline physiological data that may be output from the one or more machine learning models into the one or more LLMs, wherein generating the one or more messages may be based at least in part on inputting the one or more evaluations into the one or more LLMs.

Some examples of the method, apparatus, and non-transitory computer-readable medium described herein may further include operations, features, means, or instructions for identifying a personality type of the user based at least in part on user interactions with the application, wherein selecting the second messaging tonality may be based at least in part on identifying the personality type.

Some examples of the method, apparatus, and non-transitory computer-readable medium described herein may further include operations, features, means, or instructions for determining that the additional physiological data satisfies one or more thresholds based at least in part on comparing the additional physiological data with the baseline physiological data, wherein the second messaging tonality may be selected from the plurality of messaging tonalities based at least in part on determining the additional physiological data satisfies the one or more thresholds.

Some examples of the method, apparatus, and non-transitory computer-readable medium described herein may further include operations, features, means, or instructions for identifying a trigger condition to transition from the first messaging tonality to the second messaging tonality based at least in part on acquiring the additional physiological data, wherein selecting the second messaging tonality may be based at least in part on identifying the trigger condition.

Some examples of the method, apparatus, and non-transitory computer-readable medium described herein may further include operations, features, means, or instructions for receiving a user input comprising an age of the user, a medical history of the user, one or more tags, a user interaction with the application, user feedback associated with the one or more messages generated in accordance with the first messaging tonality, one or more modifications to the first messaging tonality, or any combination thereof, wherein selecting the second messaging tonality may be based at least in part on receiving the user input.

Some examples of the method, apparatus, and non-transitory computer-readable medium described herein may further include operations, features, means, or instructions for causing a GUI of the user device to display the one or more messages in accordance with the first messaging tonality based at least in part on generating the one or more messages and causing the GUI of the user device to display the one or more additional messages in accordance with the second messaging tonality based at least in part on generating the one or more additional messages.

Some examples of the method, apparatus, and non-transitory computer-readable medium described herein may further include operations, features, means, or instructions for causing the user device to provide a first audio output of the one or more messages in accordance with the first messaging tonality based at least in part on generating the one or more messages and causing the user device to provide a second audio output of the one or more additional messages in accordance with the second messaging tonality based at least in part on generating the one or more additional messages.

Some examples of the method, apparatus, and non-transitory computer-readable medium described herein may further include operations, features, means, or instructions for inputting the baseline physiological data into the one or more LLMs based at least in part on receiving the baseline physiological data, wherein generating the one or more messages may be based at least in part on inputting the baseline physiological data into the one or more LLMs and inputting the additional physiological data into the one or more LLMs based at least in part on acquiring the additional physiological data, wherein generating the one or more additional messages may be based at least in part on inputting the additional physiological data into the one or more LLMs.

In some examples of the method, apparatus, and non-transitory computer-readable medium described herein, the first messaging tonality may be associated with a first set of characteristics, the second messaging tonality may be associated with a second set of characteristics, and the first set of characteristics, the second set of characteristics, or both, comprise a word choice, a word arrangement, a punctuation, one or more graphical elements, a volume, a cadence, an inflection, or any combination thereof.

In some examples of the method, apparatus, and non-transitory computer-readable medium described herein, the wearable device comprises a finger-worn device, a wrist-worn device, a patch, a head-worn device, a chest-worn device, or a combination thereof.

In some examples of the method, apparatus, and non-transitory computer-readable medium described herein, the one or more processors may be located within the wearable device, within the user device, with a server, or any combination thereof.

In some examples of the method, apparatus, and non-transitory computer-readable medium described herein, the wearable device collects the baseline physiological data and the additional physiological data from the user based on arterial blood flow, capillary blood flow, arteriole blood flow, or a combination thereof.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A system for adjusting a messaging tonality of messages delivered to a user, comprising:
    a wearable ring device configured to measure physiological data from a finger of the user, the wearable ring device comprising:
        one or more temperature sensors disposed at least partially within or beneath an inner curved surface of the wearable ring device and configured to acquire skin temperature data from the user through the inner curved surface;
        one or more light-emitting components configured to emit light into a tissue of the user through the inner curved surface of the wearable ring device;
        one or more light-receiving components configured to receive, through the inner curved surface, the light emitted by the one or more light-emitting components through the tissue of the user;
        one or more processors configured to process the physiological data associated with the user, the physiological data comprising the skin temperature data and heart rate data that is based at least in part on the light received by the one or more light-receiving components; and
        a wireless communications module configured to transmit the physiological data generated by the one or more processors;
    an application associated with the wearable ring device and executable by the wearable ring device, a user device communicatively coupled with the wearable ring device, or both; and
    one or more additional processors communicatively coupled with the wearable ring device, the application, or both, wherein the one or more additional processors are configured to:
        acquire baseline physiological data measured from the user via the wearable ring device;
        generate, using one or more large language models, one or more messages to be provided to the user via the application in response to the baseline physiological data and in accordance with a first messaging tonality;
        acquire additional physiological data from the user via the wearable ring device based at least in part on providing the one or more messages to the user in accordance with the first messaging tonality;
        perform an evaluation of the first messaging tonality by comparing the additional physiological data with the baseline physiological data;
        select a second messaging tonality from a plurality of messaging tonalities based at least in part on the evaluation of the first messaging tonality, wherein the second messaging tonality is associated with the one or more large language models; and
        generate, using the one or more large language models, one or more additional messages to be provided to the user via the application in accordance with the second messaging tonality based at least in part on selecting the second messaging tonality.

2. The system of claim 1, wherein the one or more additional processors are configured to:
    acquire second physiological data from the user via the wearable ring device based at least in part on providing the one or more messages to the user in accordance with the second messaging tonality;
    perform an evaluation of the second messaging tonality by comparing the second physiological data with the baseline physiological data, the additional physiological data, or both;
    select the second messaging tonality or a third messaging tonality from the plurality of messaging tonalities based at least in part on the evaluation of the second messaging tonality; and
    generate, using the one or more large language models, one or more additional messages to be provided to the user via the application in accordance with the second messaging tonality or the third messaging tonality based at least in part on the selecting.

3. The system of claim 1, wherein the one or more messages, the one or more additional messages, or both, are generated using the one or more large language models prior to acquiring the additional physiological data from the user, wherein the one or more additional processors are further configured to:

retrieve the one or more messages that are to be provided to the user via the application from a database based at least in part on acquiring the baseline physiological data; and retrieve the one or more additional messages that are to be provided to the user via the application from the database based at least in part on acquiring the additional physiological data.

4. The system of claim 1, wherein the one or more additional processors are further configured to:

receive a physiological data set from the user, one or more additional users, or both;

determine that the physiological data set satisfies one or more thresholds;

generate, using the one or more large language models, the one or more messages that are to be provided to the user in accordance with the first messaging tonality based at least in part on the baseline physiological data, the additional physiological data, or both, satisfying the one or more thresholds; and generate, using the one or more large language models, the one or more additional messages that are to be provided to the user in accordance with the second messaging tonality based at least in part on the baseline physiological data, the additional physiological data, or both, satisfying the one or more thresholds.

5. The system of claim 1, wherein the one or more additional processors are further configured to:

input the baseline physiological data into one or more machine learning models; and input one or more evaluations of the baseline physiological data that are output from the one or more machine learning models into the one or more large language models, wherein generating the one or more messages is based at least in part on inputting the one or more evaluations into the one or more large language models.

6. The system of claim 1, wherein the one or more additional processors are configured to:

identify a personality type of the user based at least in part on user interactions with the application; and select the first messaging tonality, the second messaging tonality, or both, based at least in part on identifying the personality type, wherein generating the one or more messages is based at least in part on selecting the first messaging tonality, and wherein generating the one or more additional messages is based at least in part on selecting the second messaging tonality.

7. The system of claim 1, wherein the one or more additional processors are configured to:

determine that the additional physiological data satisfies one or more thresholds based at least in part on comparing the additional physiological data with the baseline physiological data, wherein the second messaging tonality is selected from the plurality of messaging tonalities based at least in part on determining the additional physiological data satisfies the one or more thresholds.

8. The system of claim 1, wherein the one or more additional processors are configured to:

identify a trigger condition to transition from the first messaging tonality to the second messaging tonality based at least in part on acquiring the additional physiological data, wherein selecting the second messaging tonality is based at least in part on identifying the trigger condition.

9. The system of claim 8, wherein the one or more additional processors are configured to:

receive a user input comprising an age of the user, a medical history of the user, one or more tags, a user interaction with the application, user feedback associated with the one or more messages generated in accordance with the first messaging tonality, one or more modifications to the first messaging tonality, or any combination thereof, wherein selecting the second messaging tonality is based at least in part on receiving the user input.

10. The system of claim 1, wherein the one or more additional processors are configured to:

cause a graphical user interface (GUI) of the user device to display the one or more messages via the application in accordance with the first messaging tonality based at least in part on generating the one or more messages; and cause the GUI of the user device to display the one or more additional messages via the application in accordance with the second messaging tonality based at least in part on generating the one or more additional messages.

11. The system of claim 1, wherein the one or more additional processors are configured to:

cause the user device to provide, via the application, a first audio output of the one or more messages in accordance with the first messaging tonality based at least in part on generating the one or more messages; and cause the user device to provide, via the application, a second audio output of the one or more additional messages in accordance with the second messaging tonality based at least in part on generating the one or more additional messages.

12. The system of claim 1, wherein the one or more additional processors are configured to:

input the baseline physiological data into the one or more large language models based at least in part on receiving the baseline physiological data, wherein generating the one or more messages are based at least in part on inputting the baseline physiological data into the one or more large language models; and input the additional physiological data into the one or more large language models based at least in part on acquiring the additional physiological data, wherein generating the one or more additional messages are based at least in part on inputting the additional physiological data into the one or more large language models.

13. The system of claim 1, wherein the first messaging tonality is associated with a first set of characteristics, and wherein the second messaging tonality is associated with a second set of characteristics, wherein the first set of characteristics, the second set of characteristics, or both, comprise a word choice, a word arrangement, a punctuation, one or more graphical elements, a volume, a cadence, an inflection, or any combination thereof.

14. The system of claim 1, wherein the wearable ring device comprises a finger-worn device, a wrist-worn device, a head-worn device, a chest-worn device, or a combination thereof.

15. The system of claim 1, wherein the one or more additional processors are located within the wearable ring device, within the user device, with a server, or any combination thereof.

16. The system of claim 1, wherein the wearable ring device collects the baseline physiological data and the additional physiological data from the user based on arterial blood flow, capillary blood flow, arteriole blood flow, or a combination thereof.

17. A system for adjusting a messaging tonality of messages delivered to a user, comprising:

a wearable ring device configured to measure physiological data from a finger of the user, the wearable ring device comprising:

one or more temperature sensors disposed at least partially within or beneath an inner curved surface of the wearable ring device and configured to acquire skin temperature data from the user through the inner curved surface;

one or more light-emitting components configured to emit light into a tissue of the user through the inner curved surface of the wearable ring device;

one or more light-receiving components configured to receive, through the inner curved surface, the light emitted by the one or more light-emitting components through the tissue of the user;

one or more processors configured to process the physiological data associated with the user, the physiological data comprising the skin temperature data and heart rate data that is based at least in part on the light received by the one or more light-receiving components; and a wireless communications module configured to transmit the physiological data generated by the one or more processors;

one or more memories storing processor-executable code; and one or more additional processors coupled with the one or more memories and individually or collectively operable to execute the code to:

acquire baseline physiological data measured from the user via the wearable ring device;

generate, using one or more large language models, one or more messages to be provided to the user via an application associated with the wearable ring device in response to the baseline physiological data and in accordance with a first messaging tonality;

acquire additional physiological data from the user via the wearable ring device based at least in part on providing the one or more messages to the user in accordance with the first messaging tonality;

perform an evaluation of the first messaging tonality by comparing the additional physiological data with the baseline physiological data;

select a second messaging tonality from a plurality of messaging tonalities based at least in part on the evaluation of the first messaging tonality, wherein the second messaging tonality is associated with the one or more large language models; and generate, using the one or more large language models, one or more additional messages to be provided to the user via the application in accordance with the second messaging tonality based at least in part on selecting the second messaging tonality.

18. The system of claim 17, wherein the one or more additional processors are further configured to:

acquire second physiological data from the user via the wearable ring device based at least in part on providing the one or more messages to the user in accordance with the second messaging tonality;

perform an evaluation of the second messaging tonality by comparing the second physiological data with the baseline physiological data, the additional physiological data, or both;

select the second messaging tonality or a third messaging tonality from the plurality of messaging tonalities based at least in part on the evaluation of the second messaging tonality; and generate, using the one or more large language models, one or more additional messages to be provided to the user via the application in accordance with the second messaging tonality or the third messaging tonality based at least in part on the selecting.

19. A method for adjusting a messaging tonality of messages delivered to a user, comprising:

acquiring baseline physiological data from the user via a wearable ring device configured to be worn on a finger of the user, the baseline physiological data comprising at least skin temperature data acquired through an inner curved surface of the wearable ring device via one or more temperature sensors, and heart rate data acquired via one or more light-emitting components and one or more light-receiving components of the wearable ring device;

transmitting, using a wireless communications module of the wearable ring device, the baseline physiological data to a user device, a server, or both, comprising one or more processors;

generating, using one or more large language models, one or more messages to be provided to the user via an application associated with the wearable ring device in response to the baseline physiological data and in accordance with a first messaging tonality;

acquiring additional physiological data from the user via the wearable ring device based at least in part on providing the one or more messages to the user in accordance with the first messaging tonality;

performing an evaluation of the first messaging tonality by comparing the additional physiological data with the baseline physiological data;

selecting a second messaging tonality from a plurality of messaging tonalities based at least in part on the evaluation of the first messaging tonality, wherein the second messaging tonality is associated with the one or more large language models; and generating, using the one or more large language models, one or more additional messages to be provided to the user via the application in accordance with the second messaging tonality based at least in part on selecting the second messaging tonality.

20. The method of claim 19, further comprising:

acquiring second physiological data from the user via the wearable ring device based at least in part on providing the one or more messages to the user in accordance with the second messaging tonality;

performing an evaluation of the second messaging tonality by comparing the second physiological data with the baseline physiological data, the additional physiological data, or both;

selecting the second messaging tonality or a third messaging tonality from the plurality of messaging tonalities based at least in part on the evaluation of the second messaging tonality; and generating, using the one or more large language models, one or more additional messages to be provided to the user via the application in accordance with the second messaging tonality or the third messaging tonality based at least in part on the selecting.

\* \* \* \* \*